(12) United States Patent
Banner et al.

(10) Patent No.: US 6,820,618 B2
(45) Date of Patent: *Nov. 23, 2004

(54) METHOD AND APPARATUS FOR NULLIFYING THE IMPOSED WORK OF BREATHING

(75) Inventors: Michael Joseph Banner, Alachua, FL (US); Paul Bradford Blanch, Alachua, FL (US)

(73) Assignee: University of Florida Research Foundation, Incorporated, Gainesville, FL (US)

(*) Notice: Subject to any disclaimer, the term of this patent is extended or adjusted under 35 U.S.C. 154(b) by 101 days.

This patent is subject to a terminal disclaimer.

(21) Appl. No.: 10/233,728

(22) Filed: Sep. 3, 2002

(65) Prior Publication Data

US 2003/0010339 A1 Jan. 16, 2003

Related U.S. Application Data

(63) Continuation of application No. 09/243,268, filed on Feb. 3, 1999, now abandoned.

(51) Int. Cl.[7] .......................... A61M 16/00; A62B 7/00; F16K 31/02
(52) U.S. Cl. .......................... 128/204.23; 128/204.18; 128/202.22
(58) Field of Search ....................... 128/202.22, 204.18, 128/204.21, 204.22, 204.23, 204.26, 205.23

(56) References Cited

U.S. PATENT DOCUMENTS

| 4,565,194 A | 1/1986 | Weerda et al. |
| 4,957,107 A | 9/1990 | Sipin |
| 5,316,009 A | 5/1994 | Yamada |
| 5,546,935 A | * 8/1996 | Champeau ............. 128/205.23 |
| 5,582,163 A | 12/1996 | Bonassa |
| 5,692,497 A | 12/1997 | Schnitzer et al. |
| 5,803,066 A | 9/1998 | Rapoport et al. |
| 5,941,710 A | 8/1999 | Lampotang et al. |
| 5,954,050 A | 9/1999 | Christopher |
| 6,182,657 B1 | 2/2001 | Brydon et al. |
| 6,390,091 B1 | * 5/2002 | Banner et al. ......... 128/204.21 |
| 6,450,164 B1 | * 9/2002 | Banner et al. ......... 128/204.21 |
| 6,571,796 B2 | * 6/2003 | Banner et al. ......... 128/204.26 |

FOREIGN PATENT DOCUMENTS

WO    WO 97/10868    3/1997

* cited by examiner

Primary Examiner—Henry Bennett
Assistant Examiner—Andrea M. Ragonese
(74) Attorney, Agent, or Firm—Akerman Senterfitt

(57) ABSTRACT

A method and corresponding medical ventilator for nullifying the work of breathing imposed by the ventilation breathing apparatus during ventilation support of a patient having a source of breathing gas, a pressure sensor, a microprocessor, at least one actuator of a pneumatic system, and driver circuits. The medical ventilator is in fluid communication with the source of breathing and an endotracheal tube which is in fluid communication with the lungs of the patient. At least one driver circuit adjusts at least one actuator to change the supply of the breathing gas. The pressure sensor measures the pressure of the gas proximate the distal end of the endotracheal tube and generates an output based on the sensed pressure. The microprocessor controls the supply of the breathing gas exiting the pneumatic system of the ventilator and is electrically coupled to the output of the pressure sensor. The microprocessor compares the output of the pressure sensor to a predetermined baseline pressure that is greater than zero and, as a result, adjusts the actuator so that the pressure of the gas proximate the distal end of the endotracheal tube is maintained at the predetermined baseline pressure.

36 Claims, 12 Drawing Sheets

METHOD AND APPARATUS FOR NULLIFYING THE IMPOSED WORK OF BREATHING

This application is a continuation of, and claims the benefit of, application Ser. No. 09/243,268, filed Feb. 3, 1999, which status is now abandoned, which application is hereby incorporated herein in its entirety by reference.

BACKGROUND OF THE INVENTION

1. Field of the Invention

The present invention relates to the respiratory care of a patient and, more particularly, to a ventilator that monitors the pressure of the breathing gas supplied to and exhaled from the patient, and controls the pressure and/or flow rate of the breathing gas supplied by the ventilator to the patient to nullify the work of breathing imposed on the patient by the breathing apparatus.

2. Prior Art

Mechanical ventilatory support is widely accepted as an effective form of therapy and means for treating patients with respiratory failure. Ventilation is the process of delivering oxygen to and washing carbon dioxide from the alveoli in the lungs. When receiving ventilatory support, the patient becomes part of a complex interactive system which is expected to provide adequate ventilation and promote gas exchange to aid in the stabilization and recovery of the patient. Clinical treatment of a ventilated patient often calls for monitoring a patient's breathing to detect an interruption or an irregularity in the breathing pattern, for triggering a ventilator to initiate assisted breathing, and for interrupting the assisted breathing periodically to wean the patient off of the assisted breathing regime, thereby restoring the patient's ability to breath independently.

A patient whose breathing is being supported by a ventilator typically receives breathing gas through a ventilator conduit. The ventilator conduit generally consists of two flexible conduits, an inhalation conduit and an exhalation conduit, connected to a wye fitting. The free ends of the conduits are attached to the ventilator so that the inhalation conduit receives breathing gas from the ventilator's pneumatic system and the exhalation conduit returns gas exhaled by the patient to the ventilator. The wye fitting is typically connected to the patient's breathing attachment, which is oftentimes an endotracheal tube, which conducts breathing gas into the lungs of the patient, and exhaled gas from the lungs of the patient to the exhalation conduit.

In those instances where a patient requires mechanical ventilation due to respiratory failure, a wide variety of mechanical ventilators are available. Most modern ventilators allow the clinician to select and use several modes of inhalation either individually or in combination. These modes can be defined in three broad categories: spontaneous, assisted or controlled. During spontaneous ventilation without other modes of ventilation, the patient breathes at his own pace, but other interventions may affect other parameters of ventilation including the tidal volume and the baseline pressure, above ambient, within the system. In assisted ventilation, the patient initiates the inhalation by lowering the baseline pressure, and then the ventilator "assists" the patient by completing the breath by the application of positive pressure. During controlled ventilation, the patient is unable to breathe spontaneously or initiate a breath, and is therefore dependent on the ventilator for every breath.

During spontaneous or assisted ventilation, the patient is required to "work" (to varying degrees) by using the respiratory muscles in order to breath. The work of breathing can be measured and quantified in Joules/L of ventilation. In the past, techniques have been devised to supply ventilatory therapy to patients for the purpose of improving patient efforts to breath by decreasing the work of breathing to sustain the breath. Still other techniques have been developed that aid in the reduction of the patient's inspiratory work required to trigger a ventilator system "ON" to assist the patient's breathing. It is desirable to reduce the effort expended by the patient in each of these phases, since a high work of breathing load can cause further damage to a weakened patient or be beyond the capacity or capability of small or disabled patients.

The work of breathing of a patient breathing spontaneously while intubated and attached to the ventilator during ventilatory support by may be divided into two components: first, the imposed work of breathing of the breathing apparatus; and second, the physiologic work of breathing of the patient. The imposed work of breathing is the resistive work of breathing imposed by the breathing apparatus (the physical construct of the entire ventilation support external to the patient' lungs, i.e., the endotracheal tube, the ventilator conduit, the medical ventilator, etc.) upon the spontaneously breathing patient receiving ventilator support. The physiologic work of breathing of the patient consists of two components: first, the resistive work of breathing of the airways of the patient, and two, the elastic work of breathing of the lungs and the chest wall. It is desirable to reduce or, even more desirable, to nullify the imposed work of breathing as the patient may be detrimentally affected by an excessively high expenditure of energy early in the inspiration process caused by the respiratory muscle force required to overcome the imposed work of breathing of the breathing apparatus. Patient's may fatigue under the imposed work of breathing workload which predisposes the patient to respiratory muscle fatigue, respiratory distress, respiratory or ventilator dependancy, and/or failure. Nullification of the imposed work of breathing also allows for the contemporaneous determination of the physiologic work of breathing.

The conventional methods and apparatus for reducing or minimizing the imposed work of breathing are inadequate. Typically, these conventional efforts rely upon a means of "triggering" the ventilator to supply inspiratory ventilation support upon the sensing of an inspiration effort. The conventional means for triggering the ventilator may be classified as either pressure or flow-by triggering. In conventional pressure triggering, the withdrawal of the small volume of gas that occurs as a breath is initiated by the patient results in a corresponding drop in pressure which is monitored via a pressure sensor that is typically disposed within the ventilator conduit at or near the wye piece or within either the inhalation conduit or the exhalation conduit. At the onset of spontaneous inhalation by the patient, the pressure change is detected in the breathing circuit which functions to trigger the ventilator "ON" to then actively inflate the lungs of the patient during ventilation support. Several disadvantages are associated with the use of conventional pressure triggering to reduce the imposed work of breathing. First, the chosen pressure measurement sites produce a pressure signal that measures the pressure of the breathing gas proximate the sensors which is remote from the actual intratracheal pressure drop occurring within the patient's trachea throughout the spontaneous inhalation effort. The measured sensors are then used as a basis for regulating or controlling the amount of pressure or flow rate (to generate the requisite pressure) of breathing gas applied to the lungs. Because the chosen sites are so remote from the lungs of the patient, the resulting pressure measurements are an inherently inaccurate measurement of the pressure on the airways and lungs of the patient which causes a marked increase in the effort or work to inhale by the patient as the regulated amount of breathing gas applied to the patient is calculated in error due to the "approximated" value of the pressure drop sensed.

Second, and once again because of the remote pressure sensing measurement sites, in conventional pressure triggering there is a significant amount of lag time and associated negative pressure that always occurs between the onset of the patient's inspiratory effort and the time that the gas pressure or flow reaches the patient's airway. This lag time is generally referred to as a ventilator's response time, and commonly occupies a small but significant portion of a patient's total inspiration time. The pressure waves that are indicative of the pressure drop travel to the pressure sensor at the speed of sound in the breathing gas, which is approximately 1 millisecond per foot. Due to factors inherent in conventional ventilator design and the prior art locations of the pressure sensing site, the resulting patient inspiration effort can typically continue for as long as 40 to 500 milliseconds without ventilator assistance. Thus, under the conventional pressure drop triggering schemes, the pressure drop, which a patient is required to create in order to trigger a breath in a closed breathing circuit, can require a significant expenditure of energy by the patient. This imposed work of breathing on the patient can be detrimental in that respiratory muscles already loaded and nearly fatigued by an operation or other patient conditions may continue to fatigue, which, if this process continues, may result in the failure or severe compromise of the ventilation support procedure. Additionally, the forced respiratory work required to trigger ventilation may be beyond the capacity of infant, small children, or patients' suffering from trauma or disease.

In flow-by triggering, the signal to cycle "ON" the ventilator to deliver pressure or flow support of a patient's inhalation effort is determined by monitoring the flow in the patient's ventilator conduit or inside the ventilator. In such a system, a single flow sensor is typically positioned inside the ventilator to monitor the flow of gas that a patient withdraws from the ventilator system via the ventilator conduit and triggers a pressure or flow based breath support when the patient's inspiratory flow equals a certain level. However, such a closed system flow based trigger is not an improvement over a conventional pressure triggering system, because all of the same delays and work required of the patient (imposed on the patient) are still present. In addition, a significant negative pressure drop is still required to start the breath and there is no continuous flow to support the earliest phase of the breath. Significantly, even if there were some form of continuous flow to support the earliest phase of the breath in an effort to minimize the imposed work of breathing required of the patient to cause the requisite negative pressure drop, the remote location of the flow sensor would still cause inappropriate application of the pressure or flow based breath support due to the inherent inadequacy of the measurement site. Therefore, in conventional triggering means developed to minimize the imposed work of breathing of the patient, the patient must still overcome the substantial resistance and inertia of the breath triggering process. The present invention overcomes the prior art limitations, and due to the diminimus response time, aids in reducing and effectively nullifying the imposed work of breathing of the patient.

Optimal ventilatory assistance requires a balance between appropriately minimizing physiologic workloads to a tolerable level and decreasing imposed resistive workloads to zero. This balance should insure that the patient is neither overstressed nor oversupported. Insufficient ventilatory support places unnecessary demands upon the patient's compromised respiratory system, thereby inducing or increasing respiratory muscle fatigue. Excessive ventilatory support places the patient at risk for pulmonary-barotrauma and other complications of mechanical ventilation.

From the above, it is clear that it would be desirable to have a medical ventilator that reduces, and effectively nullifies, the patient's imposed work of breathing. Further, it is clear that it would be desirable to have a medical ventilator that can supply a clinician's desired mode or technique of spontaneous or assisted ventilation support while contemporaneously nullifying the imposed work of breathing of the patient. Such a medical ventilator is unavailable in current systems.

SUMMARY

An excessively high expenditure of energy (work of breathing) by the patient, early in the inspiratory process, can be detrimental to the patient. Patients may fatigue under these workloads, leading to further respiratory distress and/or failure. The required energy expenditure can also create difficulties in weaning the patient from the ventilator, leading to patients who become ventilator dependent. Thus, reducing the energy expenditure of the patient to an appropriate level and minimizing or eliminating unnecessary energy expenditures while breathing on a mechanical ventilator is advantageous for the patient.

Few improvements have been made in the reduction of the work of breathing imposed by the ventilation breathing apparatus (the physical construct of the entire ventilation support system external to the patient's lungs, i.e., the endotracheal tube, the ventilator conduit, the medical ventilator, etc.). The conventional methods and apparatus of prior art ventilators, or ventilator systems, for reducing or minimizing the imposed work of breathing are inadequate and require the patient to unnecessarily expend a significant amount of energy in an effort to overcome the imposed work of breathing to initiate the desired ventilation support. This imposed work of breathing on the patient can be detrimental in that the patient's respiratory muscles, which may be already loaded and nearly fatigued by an operation or other patient conditions, may continue to fatigue and, if this process continues, may lead in the failure or severe compromise of the ventilation support procedure. The principle object of the present invention is to provide a method and corresponding apparatus for nullifying the work of breathing imposed by the ventilation breathing apparatus by continually modulating the pressure and/or flow rate of the breathing gas supplied by the ventilator to maintain the pressure of the breathing gas near the distal end of a breathing attachment, such as the preferred endotracheal tube, at a constant, predetermined, baseline pressure throughout an inhalation effort of the patient.

A further object of the present invention is to provide a method and corresponding apparatus that may be used simultaneously with pressure support ventilation methods and modes known to those skilled in the arts to improve patient efforts to breath by both reducing the work of breathing required to sustain a breath and for nullifying the work of breathing imposed by the ventilation breathing apparatus.

Briefly, the present invention is directed to a medical ventilator for supplying a breathing gas to a patient for use in a medical procedure, such as ventilation support. The breathing gas being received into the medical ventilator from a gas source of one or more breathing gases and the gas exiting the ventilator being in flow communication with a functionally open ventilator conduit. The ventilator conduit has an endotracheal tube in fluid communication with the lungs of the patient. A pressure sensor is disposed near the distal end of the endotracheal tube to sense the pressure of the breathing gas proximate the pressure sensor which is indicative of the relative intratracheal pressure of the patient. A monitoring means, such as a microprocessor, is connected to the pressure sensor to monitor the pressure, to detect when the pressure sensed deviates from a predetermined baseline pressure, and, if the pressure of the gas proximate the pressure sensor is below the predetermined baseline pressure, to generate a pressure response signal thereof, and, if the pressure of the gas proximate the pressure sensor is above the predetermined baseline pressure, to generate a termination signal thereof.

The medical ventilator also has a gas delivery means that is in fluid/flow communication with the gas source for receiving the breathing gas from the gas source. The gas delivery means regulates the pressure and/or flow rate of the breathing gas supplied to the patient. Further, the medical ventilator has a regulating means operatively coupled to the gas delivery means and the monitoring means for pressure and/or flow rate controlling the breathing gas supplied to the patient so that the pressure of the breathing gas near the distal end of the endotracheal tube is maintained at the predetermined baseline pressure. The gas delivery means comprises a pneumatic system, having at least one actuator, responsive to the monitoring means via the regulating means, for controlling the pressure and/or the flow rate of the breathing gas so that the pressure of the breathing gas near the distal end of the endotracheal tube is maintained at the predetermined baseline pressure.

The regulating means, responsive to the pressure response signal from the monitoring means that indicates that the pressure of the gas proximate the pressure sensor is below the predetermined baseline pressure, may adjust at least one of the actuators of the gas delivery means, as necessary, to increase the pressure and/or flow rate of the breathing gas delivered by the medical ventilator so that the pressure of the pressure of the gas proximate the distal end of the endotracheal tube is maintained at the predetermined baseline level. Similarly, the regulating means, responsive to the termination signal from the monitoring means that indicates that the pressure of the gas proximate the pressure sensor is above the predetermined baseline pressure, may adjust at least one of the actuators so that the pressure of the pressure of the gas proximate the distal end of the endotracheal tube is maintained at the predetermined baseline level. Preferably, the regulating means is automatically and proportionally controlled by the monitoring means.

Moreover, the present invention relates to a method of controlling, for any selected period of time, a medical ventilator providing some form of ventilation support to a patient supplied with a breathing gas from the medical ventilator for nullifying the imposed work of breathing during the ventilation of the patient. The gas being pressure and/or flow rate controlled by the ventilator, the method comprising the steps of: delivering the breathing gas from the ventilator into the lungs of the patient via a ventilator conduit having an endotracheal tube; sensing the pressure of the breathing gas within the endotracheal tube; monitoring the sensed pressure to determine when the sensed pressure deviates from a predetermined baseline pressure; regulating the breathing gas supplied by the ventilator when it is determined that the sensed pressure is less than the predetermined baseline pressure; and restoring the breathing gas supplied by the ventilator when it is determined that the sensed pressure is greater than the predetermined baseline pressure. The method may also include the further step of determining the patient physiologic work of breathing.

The above and other objects and advantages of the present invention will become more readily apparent when reference is made to the following description taken in conjunction with the accompanying drawings.

DETAILED DESCRIPTION OF THE INVENTION

Figure 1:
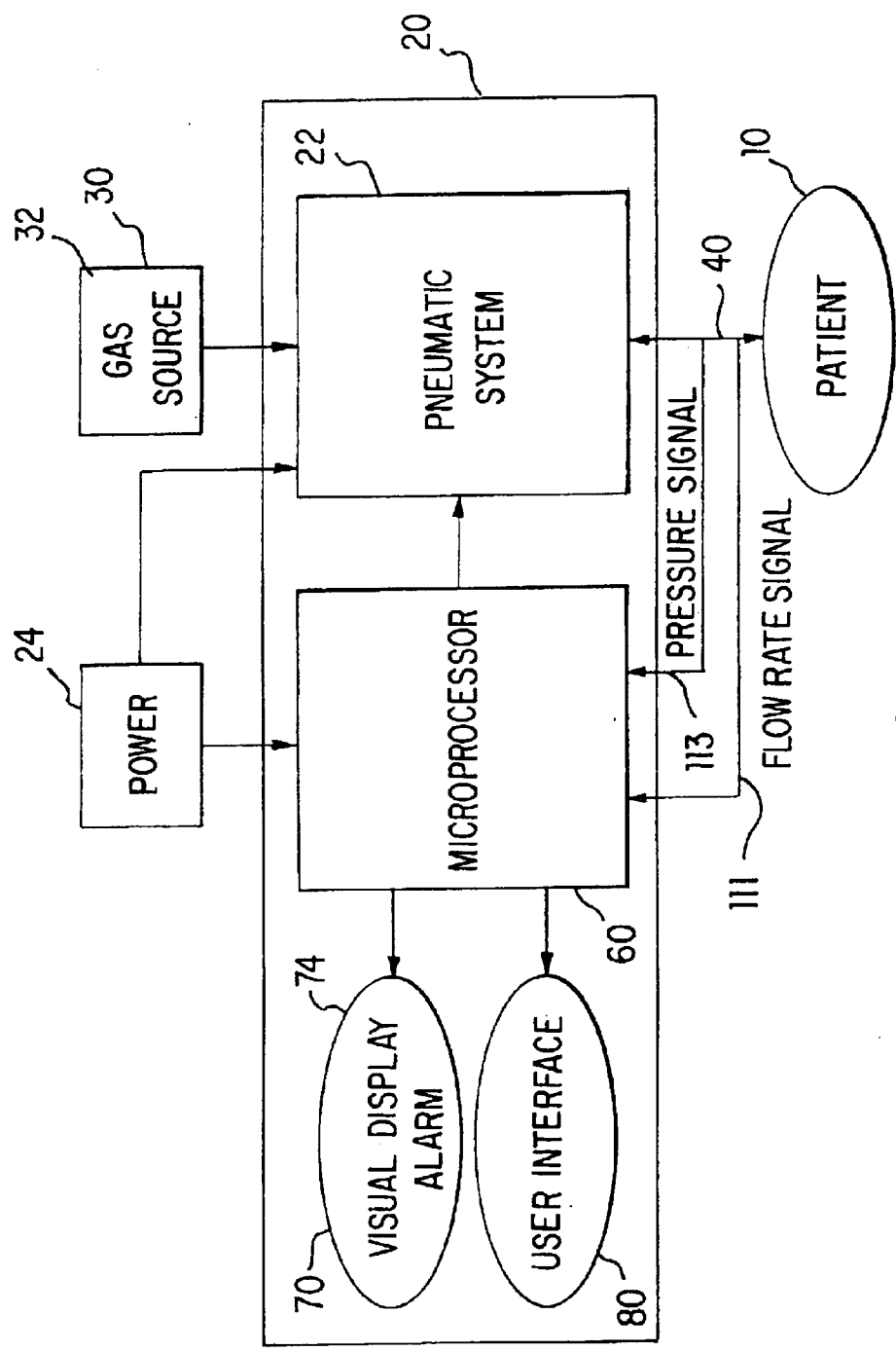
FIG. 1 is a block diagram of the medical ventilator according to the present invention.

The present invention is more particularly described in the following examples that are intended as illustrative only since numerous modifications and variations therein will be apparent to those skilled in the art. As used in the specification and in the claims, "a" can mean one or more, depending on the context in which it is used.

Pressure Support Ventilation Control

The first embodiment of the present invention is directed to a method and apparatus for providing open- or closed-loop pressure support ventilation from a ventilator 20, having a selectable pressure support ventilation level, to a patient 10, wherein the work of breathing of the patient 10 is monitored and the operating clinician is informed when the work of breathing of the patient 10 is not within a predetermined work of breathing range. The method and apparatus further provides a means to determine, and advise the operating clinician of, the pressure support ventilation level of pressure support ventilation necessary to maintain the work of breathing of the patient 10 within the predetermined work of breathing range to optimize the ventilation support provided to the patient 10. Still further, the closed-loop method and apparatus also provides a means of automatically, continually, and proportionally adjusting the pressure support ventilation level of the ventilator 20 to provide the necessary ventilator support to maintain the work of breathing of the patient 10 within the predetermined work of breathing range. It is advantageous to advise of (open-loop) and/or set (closed-loop) the pressure support ventilation level necessary to support the physiologic needs of the patient 10 because different levels of pressure support ventilation may be required whenever the patient's breathing patterns change.

As used herein, "a predetermined work of breathing range" is one that has been preset by the operating clinician. The level of pressure support ventilation may be set to partially or totally unload the respiratory muscles of the patient 10. During partial unloading, a level of pressure support ventilation is applied to decrease the patient's work of breathing to a tolerable predetermined work of breathing range. Preferably, the level of pressure support ventilation supplied to the patient 10 is increased until the work of breathing performed by the patient 10 decreases. The predetermined work of breathing range is typically not altered unless the operating clinician determines that the work of breathing range present will not provide the patient 10 with adequate ventilator support. If it is desired that the ventilation support provided by the ventilator 20 totally unloads and thus rests the respiratory muscles of the patient 10 (total respiratory muscle pressure being synonymous with a work of breathing of approximately zero), the desirable predetermined work of breathing range is typically between approximately 0.0–0.005 Joule/L. Such total respiratory muscle unloading may be appropriate to rest fatigued muscles such as in patient's with chronic respiratory failure. If it is desired that the ventilation support provided by the ventilator 20 partially unloads the respiratory muscles so that the workload imposed upon the patient 10 is tolerable and nonfatiguing, the desirable predetermined work of breathing range is typically the normal range for work of breathing, i.e., approximately 0.3 to 0.65 Joules/L. Under this condition, the workload of breathing is shared between the ventilator 20 and the respiratory muscles of the patient 10 because, during inhalation with pressure support ventilation, positive pressure actively assists in inflating the lungs 14 of the patient 10, thereby providing a portion of the work of breathing and relieving/unloading the respiratory muscles of the increased workload. As a result, as one skilled in the art will appreciate, the force and duration of muscle contraction and the work of breathing are reduced. As one skilled in the art will appreciate, any desired work of breathing range may be selected between the extremes of total unloading of the respiratory muscles (work of breathing approximately 0.0 Joule/L) and complete loading of the respiratory muscles whereby the ventilator 20 is providing no ventilator support (for example, a work of breathing of approximately 3.0 Joule/L) to act at the predetermined work of breathing range.

A "patient breathing attachment" may be any gas delivery device, such as a mask [not shown] or a tube 54, that either superimposes over or enters a body cavity 12 or space that delivers the pressure and/or flow rate controlled breathing gas 32 at a selected pressure support ventilation level into the lungs 14 of the patient 10. For the pressure support ventilation used in the present invention it is preferable that an endotracheal tube 54 be used as the patient breathing attachment 50. The endotracheal tube 54 has a proximal end 58 and an opposed distal end 56. The endotracheal tube 54 is typically inserted into the patient's mouth and thence into the patient's trachea so that the distal end 56 of the endotracheal tube 54 is disposed in the trachea before it branches into the mainstem bronchi that lead into the lungs 14 and so that the breathing gas 32 exiting the distal end 56 of the endotracheal tube 54 is in fluid communication of the patient's lung.

"Pressure support ventilation" may be a ventilation support medical procedure for supplying pressure support breaths of breathing gas 32 at a pressure support level during inspiration by a patient 10. Pressure support ventilation is advocated to unload the respiratory muscles and decrease the work of breathing and thus decrease energy demands of patients 10 with decreased compliance and/or increased resistance. It also augments spontaneous breathing by decreasing the work imposed by the resistance of the breathing apparatus. In pressure support ventilation, the ventilator 20 is patient-triggered "ON," resulting in an abrupt increase in pressure within the endotracheal tube 54 to the preselected pressure support ventilation level, which provides a positive-pressure level, resulting from a variable flow of gas 32 from the ventilator 20. As long as the patient 10 maintains an inspiratory effort, airway pressure is held constant at the preselected pressure support ventilation level. Gas flow rate from the ventilator 20 typically ceases when the patient's inspiratory flow rate demand decreases to a predetermined percentage of the initial peak mechanical inspiratory flow rate (e.g., 25%). The ventilator 20 is thus flow-cycled "OFF" during pressure support ventilation. Once the preselected pressure support level is inputted and set, the patient 10 interacts with the pressure-assisted breath and retains control over inspiratory time and flow rate, expiratory time, breathing rate, tidal volume, and minute volume. Patient 10 work decreases and ventilator work increases at incremental levels of pressure support ventilation.

A "breathing gas" may be any gas 32 supplied to the patient 10, such as pure oxygen, air mixed with oxygen, and/or medication mixed with either oxygen or oxygen and air and may also refer to the gas 32 exhaled by the patient 10. For example, a supply of oxygen can be supplemented by air, nitrogen, helium, nitrous oxide, nitric oxide, carbon dioxide, medications, or a mixture thereof.

Figure 2:
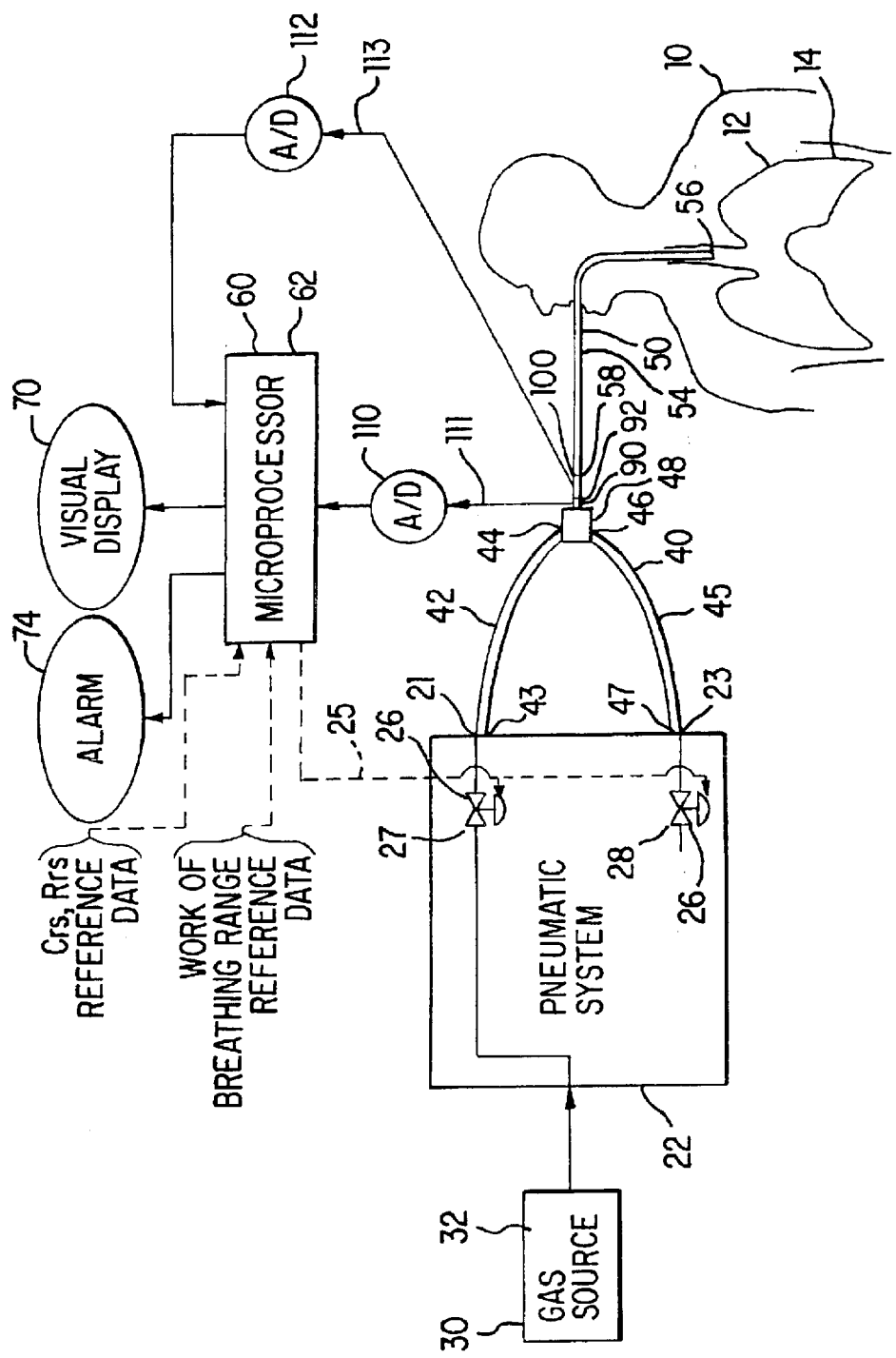
FIG. 2 is a block diagram of the medical ventilator according to the first embodiment of the present invention.

Referring to FIGS. 1 and 2, a patient is indicated at 10. The first embodiment of the present invention is a medical ventilator 20 having a selectable pressure support ventilation level, the medical ventilator 20 in flow/fluid communication with a gas source 30 of breathing gas 32 and a functionally open ventilator flow conduit 40 having a patient breathing attachment 50 in fluid communication with the lungs 14 of the patient 10. The breathing gas 32 is pressure and/or flow rate controlled by a gas delivery means of the medical ventilator 20 so that the breathing gas 32 is delivered to the patient 10 at the selected pressure support ventilation level. The ventilator further comprises a pressure sensing means disposed within the ventilator conduit 40 for sensing the pressure of the gas 32 within the ventilator conduit 40, a flow rate measuring means disposed within the ventilator conduit 40 for measuring the flow rate of the gas 32 within the ventilator conduit 40, and a monitoring means operatively connected to the pressure sensing means and the flow rate measuring means for monitoring the work of breathing of the patient 10 and operatively coupled to gas delivery system of the ventilator 20 via a regulating means for regulating the selected pressure ventilation level of the ventilator 20.

Referring now to FIG. 1, the medical ventilator 20, according to the first embodiment of the present invention, for advising of and/or providing the necessary pressure support ventilation level during pressure support ventilation is shown generally. Such a ventilator 20 is particularly useful in controlling the pressure support ventilation level supplied by the ventilator 20 so that the work of breathing of the patient 10 is maintained within the desired (i.e., the predetermined) work of breathing range. Specifically, FIG. 1 illustrates a gas delivery means, preferably a pneumatic system 22, in fluid/flow communication with a gas source 30 of one or more breathing gases 32 and a ventilator conduit 40 and in operative connection with a monitoring means, preferably a microprocessor 60. The ventilator conduit 40 is in fluid/flow communication with the lungs 14 of the patient 10. The microprocessor 60 and the pneumatic system 22 are connected to a power source 24. The microprocessor 60 may be connected to a visual display 70 for visual display of selected data and a user interface 80 for user defined control of the ventilator 20. The microprocessor 60 is also shown connected to a flow rate sensor 90, that measures the flow rate of the gas 32 within the ventilator conduit 40 and proximate the flow rate sensor 90, and a pressure sensor 100, that measures the pressure of the gas 32 proximate the pressure sensor 100, and to the pneumatic system 22 of the ventilator 20 via a regulating means.

As one skilled in the art would appreciate, the pneumatic system 22 of the medical ventilator 20 and the operative connection of that pneumatic system 22 to the source of breathing gas 32 of the ventilator 20 may be any design known in the art that has at least one actuator 26 that is capable of being operatively coupled, preferably electrically coupled, to the microprocessor 60 for pressure and/or flow rate controlling the breathing gas 32 supplied to the ventilator 20 from the gas source 30 so that the breathing gas 32 may be provided to the patient 10, during pressure support ventilation, at a selectable pressure support ventilation level which may be regulated. Such a pneumatic system 22 are disclosed in U.S. Pat. No. 4,838,259 to Gluck et al., U.S. Pat. No. 5,303,698 to Tobia et al., U.S. Pat. No. 5,400,777 to Olsson et al., U.S. Pat. No. 5,429,123, to Shaffer et al., and U.S. Pat. No. 5,692,497 to Schnitzer et al. and are incorporated by reference herein. Further, medical ventilators having pneumatic systems capable for selectably delivering pressure support ventilation levels during pressure support ventilation are commercially available. For example, the ventilator 20 and source of breathing gas 30 may be comprised of a Mallinckrodt, Nelcor, Puritan-Bennett, 7200ae, or a Bird 6400 Ventilator.

The regulating means of the ventilator 20 preferably comprises at least one driver circuit 25 electrically coupled to the monitoring means and to each actuator 26 of the gas delivery means. The driver circuits 25 adjust each actuator 26, as required, based on electrical signals received from the monitoring means, thus regulating the pressure and/or flow rate of the breathing gas 32 supplied to the patient 10. Each driver circuit may be a signal line.

Referring now to FIG. 2, an example of an embodiment of such a medical ventilator 20 is shown. Here the pneumatic system 22 of the ventilator 20 has two actuators 26, an inhalation conduit actuator 27 and an exhalation conduit actuator 28, that are operatively connected via the regulating means to the microprocessor 60. Each actuator 26 preferably defines a passage [not shown] through which the breathing gas 32 traverses and an actuator control means for adjusting the passage to change the rate of flow of the gas 32 therethrough. The regulating means adjusts the actuator control means of at least one actuator 26, if necessary, so that the pressure and/or flow of breathing gas 32 exiting the ventilator 20 through a ventilator outlet gas port is established and delivered at the selected pressure support ventilation level to the patient 10 via the ventilator conduit 40. The actuator 26 can be a binary valve, which is in either a fully open or fully closed position, or, more preferably, a proportional valve, in which the passage of the actuator 26 is opened proportionally corresponding to various desired flow rates. The proportional valve is preferably a high speed, flow regulating solenoid valve for regulating the flow of gas 32 from the gas source 30.

The medical ventilator 20 is in flow/fluid communication with the ventilator conduit 40 for delivery of the breathing gas 32 to the patient 10 at the selected pressure support ventilation level. As shown in FIGS. 1 and 2, and as one skilled in the art will appreciate, the ventilator flow conduit may be any conduit that allows for the tidal (to-and-fro) respiration of the breathing gas 32 (i.e., the conduit allows for the inhalation of the breathing gas 32 and for the exhalation of the gas 32 from the patient's lungs 14).

In the preferred embodiment however, and as shown in FIG. 2, the ventilator conduit 40 has an inhalation conduit 42, an exhalation conduit 45, and a patient breathing attachment 50. The inhalation conduit 42 provides a conduit for the flow of the breathing gas 32 from the ventilator 20 to a patient's breathing apparatus 50 during the inhalation phase of the patient's breath. The exhalation conduit 45 provides a conduit for the flow of the exhaled breathing gas 32 from the patient's breathing apparatus 50 to the ambient atmosphere or back to the ventilator 20 during the exhalation phase of the patient's breath. The inhalation conduit 42 has a first end 43 and an opposed second end 44 and the exhalation conduit 45 has a front end 46 and an opposed back end 47. The first end 43 of the inhalation conduit 42 is operatively connected to the ventilator outlet gas port 21 and the second end 44 of the inhalation conduit 42 is operatively connected to the patient breathing attachment 50. Similarly, the front end 46 of the exhalation conduit 45 is operatively connected to the patient breathing attachment 50 and the back end 47 of the exhalation conduit 45 is preferably operatively connected to a ventilator inlet gas port 23. The inhalation conduit 42 and the exhalation conduit 45 are preferable flexible and sufficiently long to permit the ventilator 20 to be placed at a convenient distance from a patient 10 undergoing ventilator breathing support.

As shown in FIG. 2, if used, the inhalation conduit actuator 27 of the ventilator 20 is preferably interposed between the source of breathing gas 30 and the inhalation conduit 42. Similarly, the exhalation conduit actuator 28 should be disposed near the ventilator inlet gas port 23 in fluid/flow communication with the gas 32 flowing from the exhalation conduit 45. The exhalation conduit actuator 28 may be preceded by a one-way valve to prevent retrograde flowing of gas 32 in the exhalation conduit 45 of the ventilator conduit 40.

As shown in FIG. 2, if an endotracheal tube 54 is used as the patient breathing attachment 50, the second end 44 of the inhalation conduit 42 and the front end 46 of the exhalation conduit 45 are operatively connected to the proximal end 58 of the endotracheal tube 54. Preferably, for ease of connection of the inhalation and exhalation conduits 42, 45 to the endotracheal tube 54, the second end 44 of the inhalation conduit 42 and the front end 46 of the exhalation conduit 45 is operatively connected to a fitting called a patient wye 48. Further, the wye fitting 48 is operatively connected to the proximal end 58 of the endotracheal tube 54. Thus, the endotracheal tube 54 and the flexible inhalation and exhalation conduits 42, 45 serve as primary intake and exhaust pathways for inhalation and exhalation gases 32 entering and leaving, respectively, the patient's body through the lungs 14.

As shown in FIGS. 1 and 2, various continuous sensing and/or measuring means are coupled to the ventilator 20 to facilitate the continuous monitoring of the work of breathing of the patient 10. Each of these means are commercially available. In the preferred embodiment of the present invention, the flow rate measuring means and the pressure sensing means are disposed within the ventilator conduit 40. For convenience and ease of connection, the flow rate measuring means is preferably disposed between the wye piece 48 and the proximal end 58 of the endotracheal tube 54. The flow rate measuring means generates a flow signal representative of the flow rate of the gas 32 proximate the flow rate measuring means. The flow signal generated from the flow rate measuring means is transmitted through a first analog-to-digital converter 110 (A/D converter) to the microprocessor 60 on flow signal line 111. Thus, the flow rate measuring means is preferably a flow rate sensor 90 and more particularly, is preferably a differential pressure analyzer 92, such as a pneumotachometer. For example, the differential pressure analyzer 92 may be comprised of a disposable, variable orifice pneumotachometer provided by Accutach, Glen Medical Products or a fixed orifice differential pressure pneumotach by Novametric Medical Systems. However, any flow rate sensor that is capable of sensing the flow rate of the gas 32 within the ventilator conduit 40 and providing a signal representative of that flow rate may be substituted for the flow rate sensor 90. A rotameter, a respirometer, or a thermistor flow sensor, such as the Calculair Portable Electronic Spirometer by Hospal Medical Corporation, could be suitable substitutes.

The pressure sensing means is preferably disposed in the flow path of the gas 32 within the endotracheal tube 54. More particularly, for convenience and ease of connection, it is preferred that the pressure sensing means be proximate the flow measuring means. The pressure sensing means generates a pressure signal representative of the pressure of the gas 32 proximate the pressure sensing means. Accordingly, the pressure sensing means is preferably a pressure sensor 100. More particularly, the pressure sensor 100 is preferably a piezoresistive pressure sensor or a solid state pressure transducer. Still more preferred, if the flow measuring means is the preferred differential pressure analyzer 92, the differential pressure analyzer 92 may also concurrently sense the pressure of the gas 32 proximate the differential pressure analyzer 92, thereby acting as the pressure sensor 100, and generate the requisite pressure signal. This is preferred as it requires only one sensor, the differential pressure analyzer 92, to act as both the flow measuring means and the pressure sensing means and it allows the flow rate and pressure data gathering to be accomplished at a single site in the ventilator conduit 40.

The pressure signal from the pressure sensor 100 is transmitted through a second A/D converter 112 to the microprocessor 60 on pressure signal line 113. This pressure signal may be transmitted through a digital or analog anti-aliasing filter [not shown] to remove noise above the Nyquist frequency before processing by the first A/D converter. The pressure sensor 100 may, for example, be comprised of commercially available pressure sensors from Honeywell or Sensym. However, it must be noted that any pressure sensor 100 capable of sensing the pressure of the gas 32 proximate the pressure sensor 100 and providing a signal representative of that pressure sensed could be substituted as the pressure sensor 100. For example, an aneroid pressure manometer could be a suitable substitute.

While a first and a second A/D converter 110, 112 are described for use with the flow rate sensor 90 and the pressure sensor 100 respectively, it is preferred that a single, multiplexed A/D converter [not shown] be used for converting the respective flow signal and pressure signal to digital format.

The monitoring means is responsive to the output of the pressure sensing means and the flow rate measuring means (i.e., the pressure signal and the flow rate signal respectively). The overall goal of the monitoring means is to advise of and/or maintain the most effective pressure support ventilation level for a ventilator 20 providing a patient 10 with pressure support ventilation while minimizing pressure related pulmonary and cardiovascular compromise. Specifically, as shown in FIGS. 1–8, the selected pressure ventilation level is determined, in the open-loop operation, and then alternatively automatically set, in the closed-loop operation, so that the work of breathing of the patient 10 may be maintained within a predetermined work of breathing range.

Preferably, the monitoring means is a microprocessor 60 that is electrically coupled to the flow rate sensor 90 used as a flow rate measuring means via flow signal line 111 and to the pressure sensor 100 used as a pressure sensing means via pressure signal line 113. The microprocessor 60 may be analog or digital and should contain circuits to be programmed for performing mathematical functions such as waveform averaging, amplification, linearization, signal rejection, differentiation, integration, addition, subtraction, division and multiplication, where desired. Circuits or programs for performing these functions are conventional and well known, and they form no part of the present invention. A microprocessor 60 is preferred over dedicated analog or digital processors because it has the flexibility to be programmed to store and analyze data and to provide hard copy in many forms. If an analog microprocessor 60 is used, the first and second A/D converters or the single, multiplexed A/D converter are not required, because the analog microprocessor 60 requires the flow signal and the pressure signal to be in the nonconverted analog format.

The parameters and data derived from the signals produced by the flow rate sensor 90 and the pressure sensor 100 as stored in the memory 62 of the microprocessor 60 at user-defined rates for as-needed retrieval and analysis. The flow rate and pressure sensors 90, 100 may continually monitor/sense the flow rate and the pressure of the breathing gas 32 proximate the respective sensors. The parameters and data may include: pressure, peak inflation pressures (PIP), flow rate, peak inspiratory flow rate, respiratory muscle pressure (Pmus(t)), average respiratory muscle pressure during the inspiratory period ($Pmus_{avg}(t)$), average respiratory muscle pressure over a serial number of breaths ($Pmus_{avgN}(t)$), static elastic recoil pressure (ERP), inspiratory tidal volume, baseline airway pressure, PEEP, mean airway pressure, spontaneous and ventilation breathing frequency, and spontaneous, ventilator, and total minute ventilation. The memory 62 may be, for example a floppy disk drive or hard drive of the associated microprocessor 60. These patient data may be stored to provide a permanent log of all events related to the patient's course on the ventilator 20, and allow for on-line and retrospective analysis of pulmonary function, i.e., compliance of the respiratory system (Crs), resistance of the respiratory system (Rrs), and gas 32 analysis as a function of time. Furthermore, the microprocessor 60 can perform operator-specific physiologic calculations on-line and in real-time, such as the calculation of the work of breathing and the average respiratory muscle pressure of the patient 10. Alternatively, these can be stored for later analysis and review.

The circuitry for monitoring the work of breathing of the patient 10 can be embodied by other circuitry well know in the art. In addition, while the monitoring means has been described as having a single microprocessor 60 for monitoring signals representing pressure and flow rate of the gas 32 proximate the respective sensors, and for controlling the selectable pressure support ventilation level of the ventilator 20, it should be understood that two or more microprocessors 60 could be used dedicated to the individual functions. In addition, the functions of the microprocessor 60 could be achieved by other circuits, such as an application specific integrated circuit (ASIC), digital logic circuits, a microcontroller, or a digital signal processor.

Further, the microprocessor 60 may have a user interface 80 which, in the preferred embodiment, is a membrane keypad, a keyboard, or other suitable input device. An operator of the ventilator may provide the microprocessor 60, via the user interface 80, with any number of desirable input parameters, such as patient identification information, patient age, patient weight, patient health, or any other desired patient statistics. However, at minimum, the operating clinician must input the desired predetermined work of breathing range so that the microprocessor 60 may compare the determined work of breathing derived from the flow rate sensor 90 and the pressure sensor 100 to the predetermined work of breathing range input therein. Predetermined inspiratory reference data, such as the Crs and Rrs of the respiratory system, may also be input into the microprocessor 60.

The ventilator 20 may further have a visual display 70, electronically coupled to the monitoring means for outputting and displaying electronic output signals generated from the monitoring means. The preferred electronic output signals may include at least one of: the signal data, the determined tidal volume, the determined respiratory muscle pressure (Pmus(t)), the determined average respiratory muscle pressure during the inspiratory period ($Pmus_{avg}(t)$), the determined average respiratory muscle pressure over a serial number of breaths ($Pmus_{avgN}(t)$) average tidal volume, the average peak inspiratory muscle pressure, the average respiratory muscle pressure, the work of breathing of the patient 10, the selected pressure support ventilation level, the target pressure support ventilation level, and the initial value of the selected pressure support level for concurrent review by the operator of the ventilator 20. The visual display 70 may vary the pattern of the display in accordance with the contents of the electronic output signals from the monitoring means. Preferably, the visual display 70 is a monitor but any means for displaying electronic output signals known to one skilled in the art may be used.

Still further, the ventilator 20 may have an alarm means for alerting the operator of either a failure in the ventilator 20, such as a power failure, or an inappropriate ventilator support setting, such as a pressure support ventilation level that does not maintain the work of breathing of the patient 10 within the desired predetermined work of breathing range. Preferably, the alarm means comprises a visual and/or audio alarm 74 but any means for alerting the operating clinician known to one skilled in the art may be used. Of course, it is desired to use a backup power supply, such as a battery.

Figure 3:
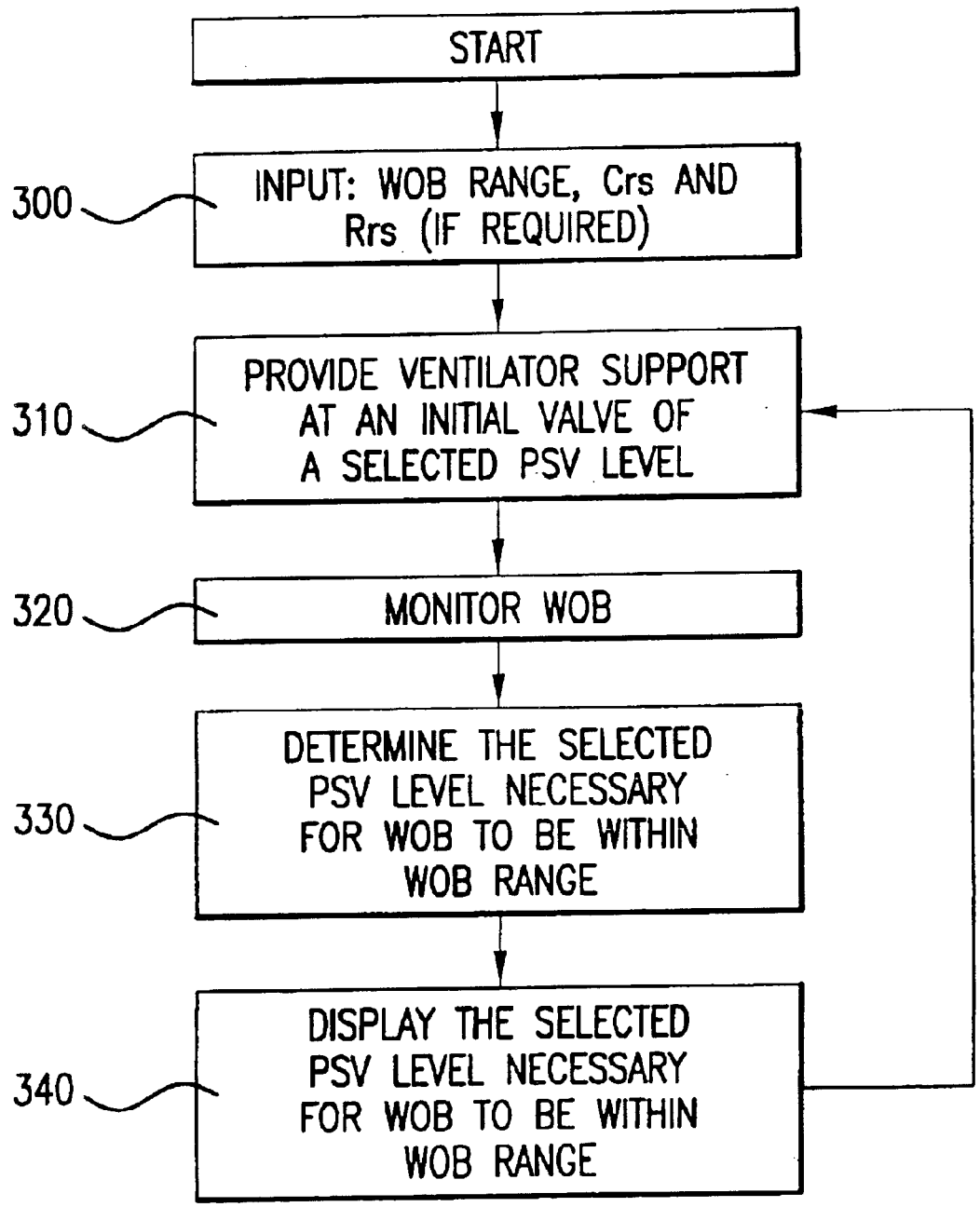
FIG. 3 is a flow chart illustrating a general sequence of steps for carrying out the open-loop operation of the first embodiment of the present invention.

Referring now to FIG. 3, in the open-loop operation of the first embodiment of the present invention, the monitoring means is responsive to the pressure signal and the flow signal to continually determine the work of breathing of the patient 10. The monitoring means compares the determined work of breathing of the patient 10 to a predetermined work of breathing range and generates a response signal based on the comparison. The monitoring means generates the response signal when the patient's work of breathing is not within the predetermined work of breathing range. Then, in response to the response signal of the monitoring means, the alarm means may generate an alarm that is suitable for alerting an operator that the patient's work of breathing is not within the predetermined work of breathing range, and the monitoring means may store the selected pressure support ventilation level as an initial value of the selected pressure support ventilation level. Still in response to the response signal of the monitoring means, the regulating means adjusts at least one of the actuators 26 of the pneumatic system 22 of the ventilator 20, if necessary, to adjust the selected pressure support ventilation level of the breathing gas 32 supplied to the patient 10. Thus, the regulating means, which is responsive to the response signal, increments the selected pressure support ventilation level provided by the ventilator 20 if the patient's work of breathing is greater than the predetermined work of breathing, or decrements the selected pressure support ventilation level delivered by the ventilator 20 if the patient's work of breathing is less than the predetermined work of breathing. The regulating means may increment/decrement the selected pressure support ventilation level by a constant level value, such as 1 or 2 PSV units, or by a variable level value based on the proportional difference between the work of breathing of the patient 10 and the predetermined work of breathing range. This incrementing and/or decrementing process continues until a selected pressure support ventilation level is reached wherein the patient's work of breathing is within the predetermined work of breathing range.

The monitoring means also detects when the patient's work of breathing is within the predetermined work of breathing range and generates a level signal in response thereto. The monitoring means, in response to the level signal, stores the selected pressure support ventilation level as a target pressure support level which is indicative of the pressure support ventilation level, during pressure support ventilation, which will provide the patient 10 with a work of breathing within the desired predetermined work of breathing range. This target pressure support level is displayed to the operator to advise them of the appropriate pressure support level. In the open-loop operation, in response to the level signal of the monitoring means, the regulating means then adjusts at least one of the actuators 26 of the pneumatic system 22 of the ventilator 20, if necessary, to adjust, by increments or decrements, the selected pressure support ventilation level of the breathing gas 32 supplied to the patient 10 so that the selected pressure support ventilation level is brought back to the initial selected pressure support ventilation level.

Thus, in the open-loop operation of the first embodiment of the present invention, upon the input of the desired predetermined work of breathing range (and the predetermined compliance and resistance of the respiratory system, if required) in Block 300, the ventilator 20 begins to provide pressure support ventilation at an initial value of the selected pressure support ventilation level, as shown in Block 310. The monitoring means, in Block 320, then monitors the work of breathing of the patient 10 and, when the work of breathing is not within the desired work of breathing range, determines, in Block 330, the target pressure support ventilation level that would maintain the patient's work of breathing within the desired predetermined work of breathing range. Concurrent with the determination of the target pressure support ventilation level, the operator may be alerted via the alarm means that the selected pressure support ventilation level is not providing pressure support ventilation that maintain the patient's work of breathing within the predetermined work of breathing range (i.e., the ventilator 20 is not providing the quality and/or quantity of pressure support ventilation necessary for the patient's current pathophysiology). Subsequent to the determination of the target pressure support ventilation level, the operator, in Block 340, is advised of the target pressure support ventilation level that will bring the patient's work of breathing within the desired range. However, as shown in FIG. 3, in the open-loop operation, the monitoring means of the ventilator 20 then steps back to block 310 to provide pressure support ventilation at the selected pressure support level that existed prior to the adjustment of the selected pressure support ventilation level in response to the response signal (i.e., back to the initial pressure support ventilation level). The monitoring means continues to monitor the patient's work of breathing and advise the operator of the target pressure support ventilation level that will maintain the patient's work of breathing within the desired work of breathing range until the ventilator 20 is reset by the operator. For those medical procedures or oversight procedures that require the operating clinician to select the pressure support ventilation level supplied by the ventilator 20 to the patient 10, the open-loop operation provides the necessary safety restriction as the operator must select the target pressure support ventilation level in order for the ventilator 20 to provide pressure support ventilation at the target pressure support ventilation level.

Figure 4:
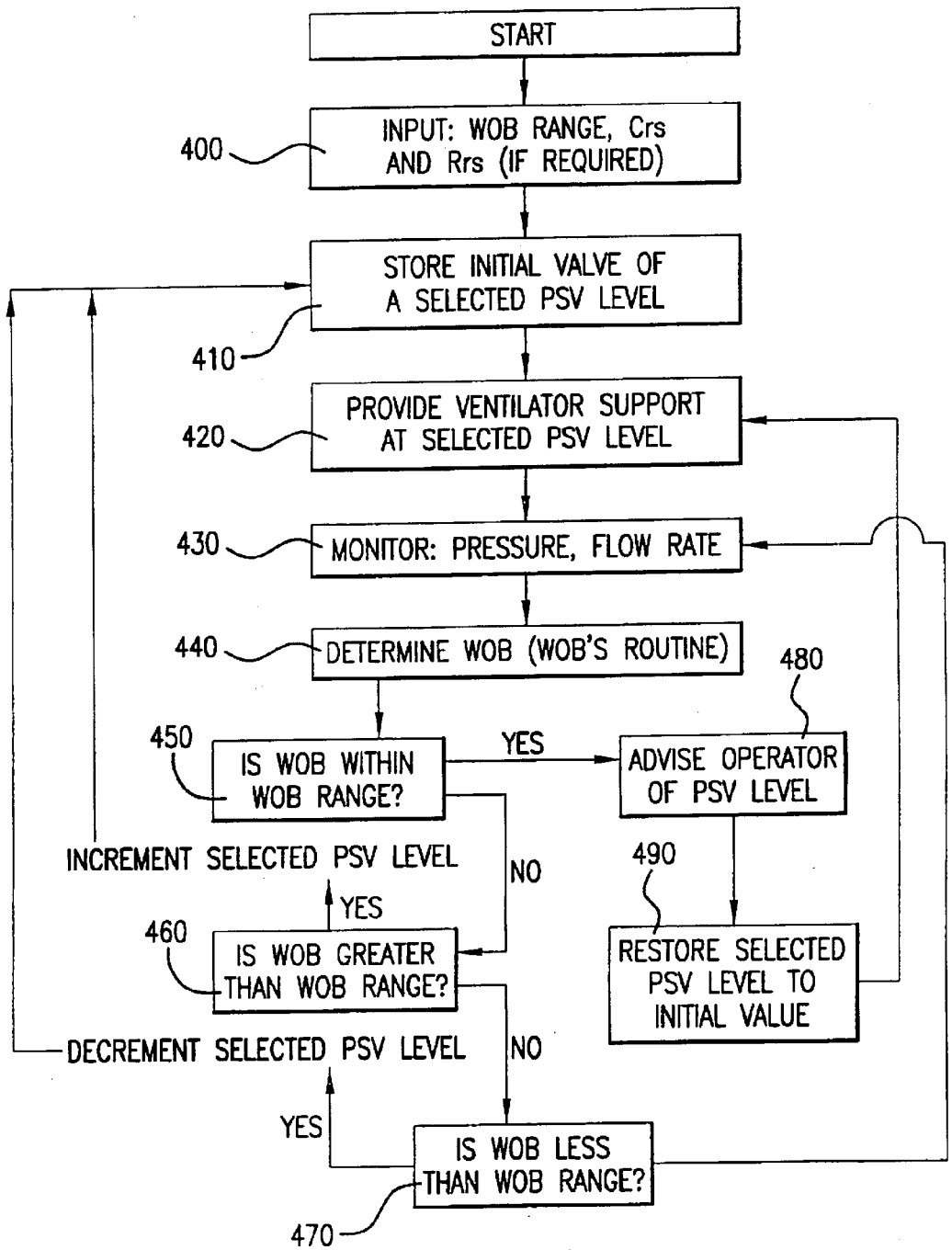
FIG. 4 is a flow chart illustrating a preferred sequence of steps for carrying out the open-loop operation of the first embodiment of the present invention.

FIG. 4 shows a flowchart for a preferred embodiment of the software that controls the open-loop operation. The program continues to execute as long as the ventilator 20 is not reset. At step 400, the input parameters are selected, such as the desired predetermined work of breathing range, the predetermined compliance and resistance of the respiratory system, if required, etc. The initial value of the selected pressure support level may also be selected, however, it is preferred that the initial value of the selected pressure support level start at zero so that the ventilator 20 can subsequently increment the pressure support ventilation level until the target pressure support ventilation level is determined. At step 410, the initial value of the selected pressure support ventilation level is stored and, in step 420, the ventilator 20 supplies breathing gas 32 to the patient 10 via the ventilator conduit 40 at the selected pressure support ventilation level. At step 430, the pressure of the breathing gas 32 is sensed and the flow rate of the breathing gas 32 is measured. At step 440, the work of breathing of the patient 10 is calculated from the sensed pressure and the measured flow rate of the breathing gas 32. In step 450, the work of breathing is monitored and, if the work of breathing of the patient 10 is not within the predetermined work of breathing range, the control algorithms in the program control the pressure support ventilation level of the ventilator 20 to selectively either increment, in step 460, when the work of breathing of the patient 10 is greater than the predetermined work of breathing range, or decrement, in step 470, when the work of breathing of the patient 10 is less than the predetermined work of breathing range, the selected pressure support ventilation level. The ventilator 20 may also alarm the operator that the patient's work of breathing is not within the desired work of breathing range. After either incrementing the selected pressure support level in step 460 or decrementing the selected pressure support ventilation level in step 470, the ventilator 20 steps back to step 420 and supplies breathing gas 32 to the patient 10 at the incremented/decremented selected pressure support ventilation level. If the selected pressure support ventilation level is not incremented or decremented in steps 460 and 470, the ventilator 20, after step 470, steps back to step 430.

However, if, in step 450, the work of breathing of the patient 10 is within the predetermined work of breathing range, the operator is advised, in step 480, of the selected pressure support ventilation level as the target selected pressure support ventilation. Further, if the selected pressure support level has been either incrementally or decrementally moved, in steps 460 and 470, from the initial value of the selected pressure support level to determine the target pressure support ventilation, in step 490, the selected pressure support ventilation level is restored to the initial value of the selected pressure support ventilation level.

Thus, preferably, in the normal operating mode of the open-loop operation of the present invention, the operator needs only to input the desired work of breathing range and, if required, the compliance and resistance of the respiratory system. The ventilator 20 then preferably applies pressure support ventilation at a low initial pressure support ventilation level, such as 0 or 2 PSV units. The ventilator 20 will then continue to incrementally increase the selected pressure support ventilation level until the work of breathing is within the desired work of breathing range. The selected pressure support ventilation that maintains the patient's work of breathing within the predetermined work of breathing range is then displayed to the operator as the target pressure support ventilation level and the selected pressure support ventilation level of the ventilator 20 is restored to deliver the pressure support ventilation at the initial pressure support ventilation level.

When the operator makes the intervention necessary in the open-loop approach, i.e., manually selecting the target pressure support ventilation level as the initial selected pressure support ventilation level, the ventilator 20 delivers the breathing gas 32 to the patient 10 at the selected pressure support ventilation level and the work of breathing of the patient 10 is monitored based on the sensed pressure and measured flow rate of the breathing gas 32 within the ventilator conduit 40. As one skilled in the art will appreciate, the ventilator 20 will continue to monitor the patient's work of breathing, continue to control the selected pressure support ventilation level of the ventilator 20, if necessary, to determine the target pressure support ventilation level by incrementing the selected pressure support ventilation level of the ventilator 20 if the patient's work of breathing is greater than the desired work of breathing range or by decrementing the selected pressure support ventilation level of the ventilator 20 if the patient's work of breathing is less than the desired work of breathing range, continue to display the target pressure support level to the operator, and continue to restore the selected pressure support ventilation level to the initial selected pressure support ventilation level until the ventilator 20 is reset.

Figure 5:
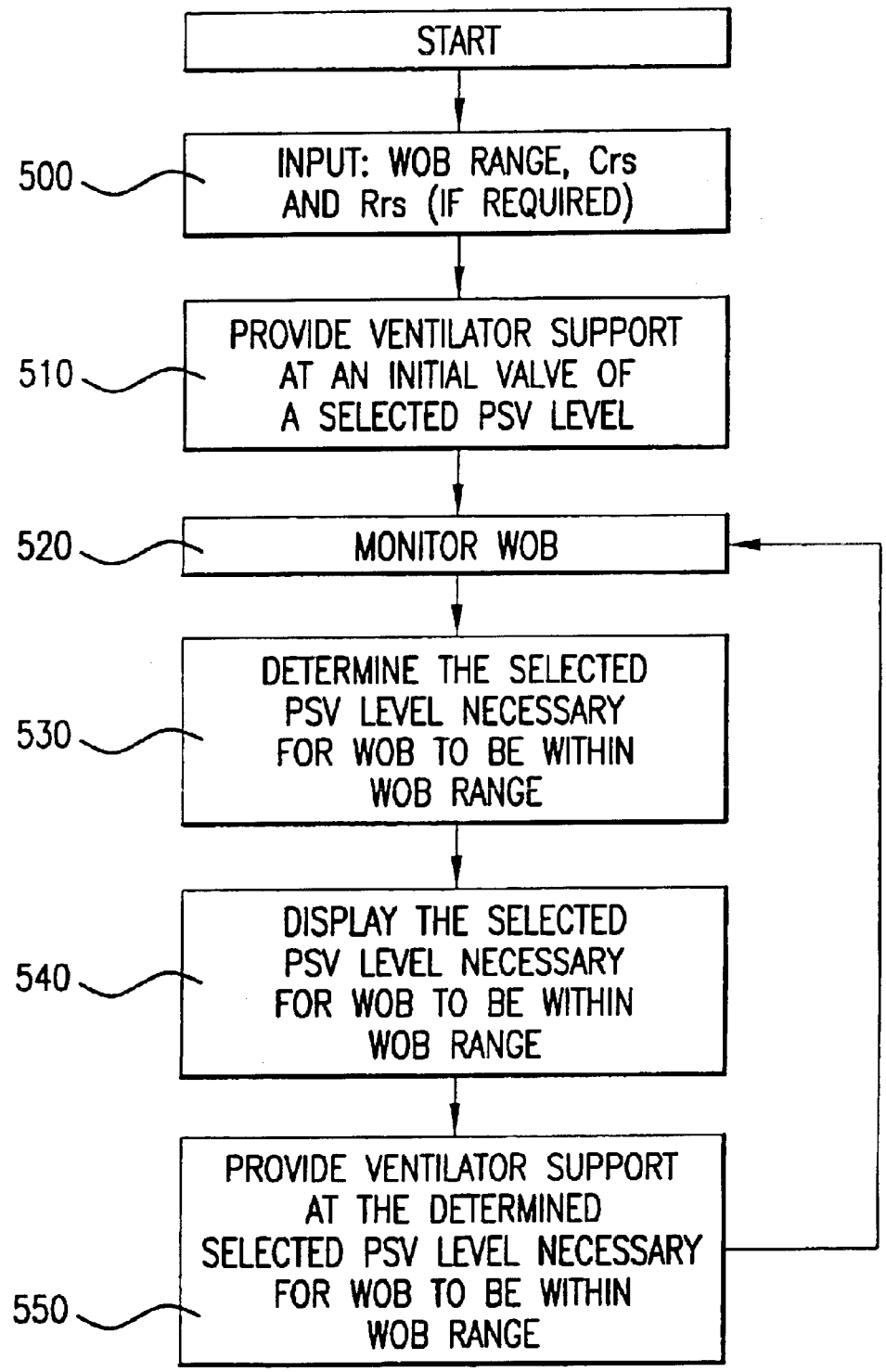
FIG. 5 is a flow chart illustrating a general sequence of steps for carrying out the closed-loop operation of the first embodiment of the present invention.

The closed-loop operation of the first embodiment of the present invention is similar to the open-loop operation with the exception that the ventilator 20 of the closed-loop operation automatically determines, sets, and delivers the pressure support ventilation level during pressure support ventilation that will maintain the patient's work of breathing within the desired predetermined work of breathing range. Referring to FIG. 5, a general overview of the closed-loop operation is shown. Just as in the open-loop operation described above, the monitoring means is responsive to the pressure signal and the flow signal to continually determine the work of breathing of the patient 10. The monitoring means compares the determined work of breathing of the patient 10 to a predetermined work of breathing range and generates a response signal based on the comparison when the patient's work of breathing is not within the predetermined work of breathing. Then, in response to the response signal of the monitoring means, the alarm means may generate an alarm that is suitable for alerting an operator that the patient work of breathing is not within the predetermined work of breathing range and the regulating means adjusts at least one of the actuators 26 of the pneumatic system 22 of the ventilator 20, if necessary, to adjust the selected pressure support ventilation level of the breathing gas 32 supplied to the patient 10. Thus, the regulating means, which is responsive to the response signal, increments the selected pressure support ventilation level provided by the ventilator 20 if the patient's work of breathing is greater than the predetermined work of breathing, or decrements the selected pressure support ventilation level delivered by the ventilator 20 if the patient's work of breathing is less than the predetermined work of breathing. The regulating means may increment/decrement the selected pressure support ventilation level by a constant level value, such as 1 or 2 PSV units, or by a variable level value which is preferably based on the proportional difference between the work of breathing of the patient 10 and the predetermined work of breathing range. This incrementing and/or decrementing process continues until a selected pressure support ventilation level is reached wherein the patient's work of breathing is within the predetermined work of breathing range.

The monitoring means detects when the patient's work of breathing is within the predetermined work of breathing range and may generate a level signal in response thereto. The monitoring means, in response to the level signal, may store the selected pressure support ventilation level as a target pressure support level which is indicative of the pressure support ventilation level, during pressure support ventilation, which will provide the patient 10 with a work of breathing within the desired predetermined work of breathing range. Further, the monitoring means may display this target pressure support level to the operator to advise them of the appropriate pressure support level currently being supplied to the patient 10 by the ventilator 20 to maintain the patient's work of breathing within the desired predetermined work of breathing range.

Thus, in the closed-loop operation, upon the input of the desired predetermined work of breathing range (and the predetermined compliance and resistance of the respiratory system, if required) in Block 510, the ventilator 20 begins to provide pressure support ventilation at an initial value of the selected pressure support ventilation level, as shown in Block 520. The monitoring means, in Block 530, then monitors the work of breathing of the patient 10 and, when the work of breathing is not within the desired work of breathing range, determines, in Block 540, the target pressure support ventilation level that would maintain the patient's work of breathing within the desired predetermined work of breathing range. Concurrent with the determination of the target pressure support ventilation level, the operator may be alerted via the alarm means that the selected pressure support ventilation level is not providing pressure support ventilation that can maintain the patient's work of breathing within the predetermined work of breathing range (i.e., the ventilator 20 is not providing the quality and/or quantity of pressure support ventilation necessary for the patient's current physiology). Subsequent to the determination of the target pressure support ventilation level, the operator, in Block 550, may be advised of the target pressure support ventilation level that has been selected by the monitoring means for delivery of the requisite level of pressure support ventilation that will bring the patient's work of breathing within the desired range. The monitoring means then, as shown in Block 560, automatically begins to delivery pressure support ventilation to the patient 10 at the target pressure support ventilation level. No intermediate or intervening actions are required from the operator for the ventilator 20 to continually monitor the work of breathing of the patient 10 and to determine and automatically deliver the appropriate pressure support ventilation level that will maintain the patient's work of breathing within the desired predetermined work of breathing range. Rather, the operator of the ventilator 20 may be simply advised that a change in the selected pressure support ventilation level has been made to adequately support the current physiological needs of the patient 10. After Block 560, the delivery of the breathing gas 32 to the patient 10 at the target pressure support ventilation level, the ventilator 20 returns to Block 520 to monitor the work of breathing of the patient 10. Blocks 520 to 560 continue until the ventilator 20 is reset by the operator. The closed-loop operation thereby provides for the automatic pressure support ventilation support in response to the changing status needs of the patient 10 by automatically setting and supplying pressures support ventilation at the selected pressure support ventilation level (i.e., the target pressure support ventilation level) that will maintain the patient's work of breathing within the desired predetermined work of breathing range.

Figure 6:
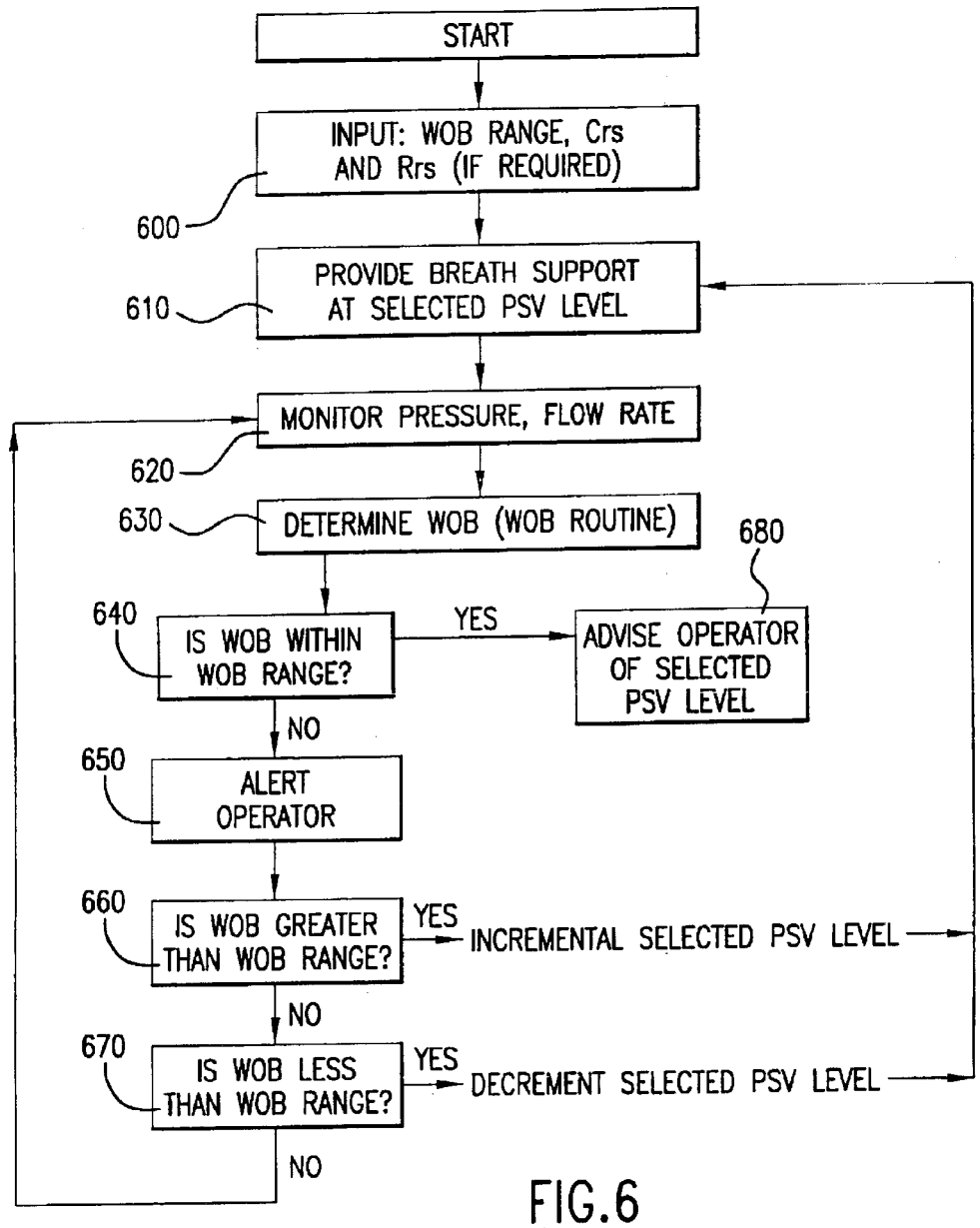
FIG. 6 is a flow chart illustrating a preferred sequence of steps for carrying out the closed-loop operation of the first embodiment of the present invention.

FIG. 6 shows a flowchart for a preferred embodiment of the software that controls the closed-loop operation of the present invention. The program continues to execute as long as the ventilator 20 is not reset. At step 600, the input parameters are selected, such as the desired predetermined work of breathing range, the predetermined compliance and resistance of the respiratory system, if required, etc. The initial value of the selected pressure support level may also be selected, however, it is preferred that the initial value of the selected pressure support level start at zero so that the ventilator 20 can subsequently increment the pressure support ventilation level until the target pressure support ventilation level is determined. At step 610, the ventilator 20 supplies breathing gas 32 to the patient 10 via the ventilator conduit 40 at the selected pressure support ventilation level. At step 620, the pressure of the breathing gas 32 is sensed and the flow rate of the breathing gas 32 is measured. At step 630, the work of breathing of the patient 10 is calculated from the sensed pressure and the measured flow rate of the breathing gas 32. In step 640, the work of breathing is monitored and if the work of breathing of the patient 10 is not within the predetermined work of breathing range, the operator may be alarmed in step 650 that the patient's work of breathing is not within the desired work of breathing range and the control algorithms in the program control the pressure support ventilation level of the ventilator 20 to selectively either increment, in step 660, when the work of breathing of the patient 10 is greater than the predetermined work of breathing range, or decrement, in step 670, when the work of breathing of the patient 10 is less than the predetermined work of breathing range, the selected pressure support ventilation level. After either steps 660 or 670, the ventilator 20 then steps back to step 610 and supplies breathing gas 32 to the patient 10 at the incremented/decremented selected pressure support ventilation level. If, in step 640, the work of breathing of the patient 10 is within the predetermined work of breathing range, the operator may be advised, in step 680, of the selected pressure support ventilation level as the target selected pressure support ventilation and the ventilator 20 steps back to step 620.

Thus, in the normal operating mode of the closed-loop operation, the operator needs only to input the desired work of breathing range and, if required, the compliance and resistance of the respiratory system. The ventilator 20 then preferably initiates pressure support ventilation at a low initial pressure support ventilation level, such as 0 or 2 PSV units. The ventilator 20 will then continue to incrementally increase the selected pressure support ventilation level until the work of breathing is within the desired work of breathing range. The selected pressure support ventilation that maintains the patient's work of breathing may then be displayed to the operator as the target pressure support ventilation level. Upon determination of the target pressure support ventilation level, the ventilator 20 automatically delivers the breathing gas 32 to the patient 10 at the selected target pressure support ventilation level corresponding to the target pressure support ventilation level without need for operator intervention.

As one skilled in the art will appreciate, the closed-loop operation will continue to monitor the patient's work of breathing, to control the selected pressure support ventilation level of the ventilator 20, if necessary, to determine the target pressure support ventilation level by incrementing the selected pressure support ventilation level of the ventilator 20 if the patient's work of breathing is greater than the desired work of breathing range or by decrementing the selected pressure support ventilation level of the ventilator 20 if the patient's work of breathing is less than the desired work of breathing range, and continue to supply pressure support ventilation to the patient 10 at the selected pressure support ventilation level corresponding to the target pressure support ventilation level until the ventilator 20 is reset.

As one skilled in the art will further appreciate, the work of breathing can be derived from the pressure signal and the flow signal by any means know to the art. However, in response to the inadequacies of the conventional approaches of applying pressure support ventilation which depend on either assessing a patient's breathing pattern or of directly measuring the work of breathing of the patient 10 which are either inaccurate or difficult to measure, it is preferred that the work of breathing of the patient 10 be derived from the average respiratory muscle pressure of the patient 10. Therefore, it is preferred that the monitoring means is responsive to the pressure signal and the flow signal to continually determine the respiratory muscle pressure of the patient 10 and then to continually determine the average respiratory muscle pressure of the patient 10 over a selected number of serial breaths. To simply and enhance the accuracy of the calculation of the work of breathing of the patient, the present invention may depend on the determination of the average respiratory muscle pressure to act as an accurate surrogate of the work of breathing of the patient 10. The respiratory muscle pressure is significantly easier to measure then the direct measure of the work of breathing of the patient 10 and is determined from routinely measured data.

Figure 7:
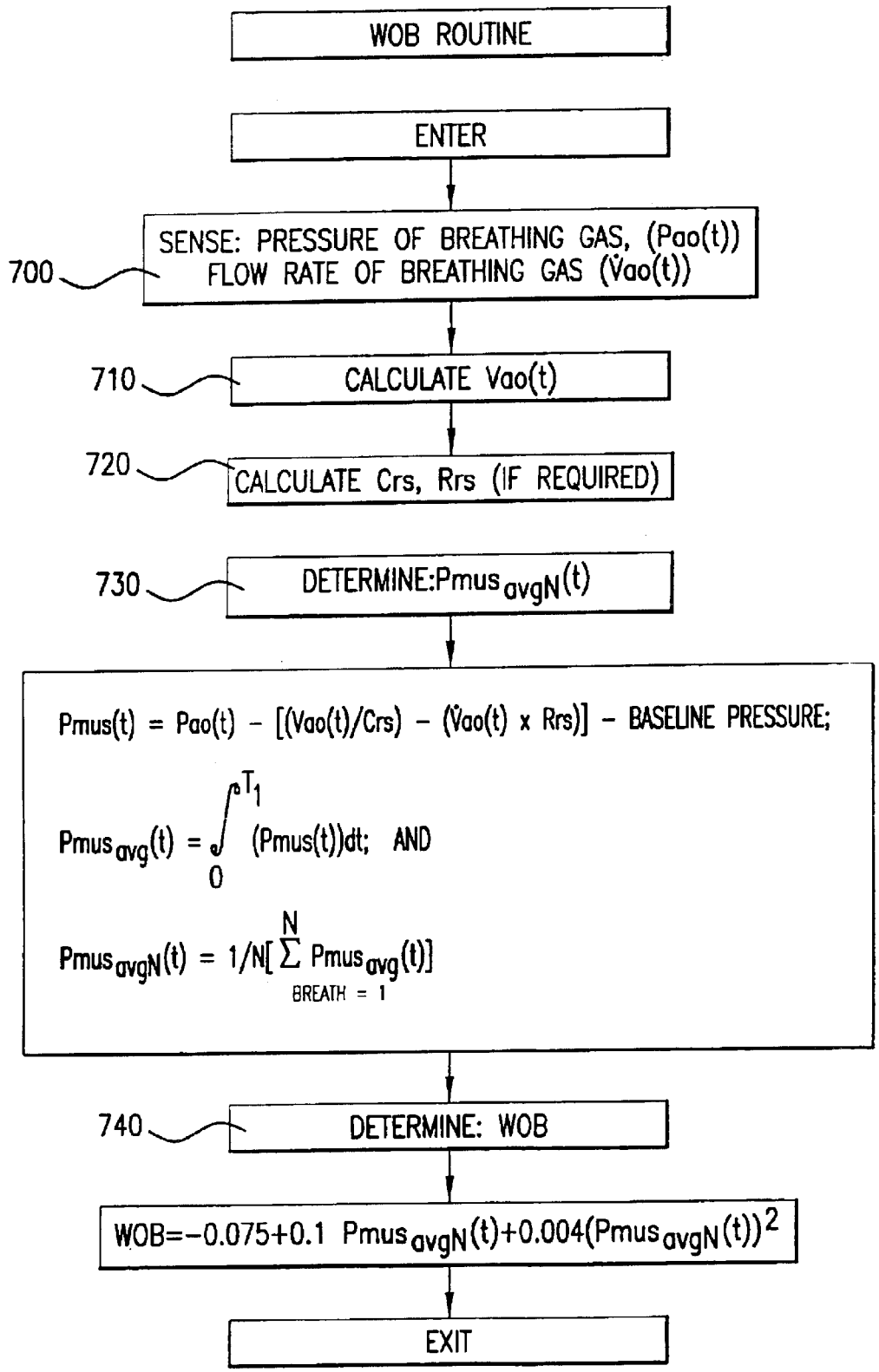
FIG. 7 is a flow chart illustrating the preferred sequence for carrying out the determination of the average respiratory muscle pressure and the work of breathing of the patient.

The preferred embodiment of the method for continuously measuring the work of breathing of the patient 10 from the average respiratory muscle pressure of the patient 10 with the ventilator 20 of the present invention is illustrated in FIGS. 4, 6, and 7. First, the flow rate sensor 90 and the pressure sensor 100 are positioned so that they are disposed in the flow path of the gas 32 within the ventilator conduit 40. Preferably, the flow rate sensor 90 is interposed, for convenience, between the wye piece 48 and the proximal end 58 of the endotracheal tube 54 and the pressure sensor 100 is disposed in series next to the flow rate sensor 90 at the proximal end 58 of the endotracheal tube 54. If a differential pressure analyzer 92 is used as a flow rate sensor, the differential pressure analyzer 92 may operate as both the pressure sensor 100 and the flow rate sensor 90, if desired, as the differential pressure analyzer 92 has the inherent capacity to generate both the requisite pressure signal and the flow signal.

Next the measurement process is started by enabling the microprocessor 60. When the measurement process is started, as shown in steps 420, 610 and 700, the flow rate sensor 90 measures, preferably continuously, the flow rate of the breathing gas 32 within the ventilator conduit 40 and generates a flow signal representative of that flow rate which is transmitted toward the processor 60 via line 111. If required, the flow signal is then digitized by the first A/D converter 110 operating at an appropriate sampling frequency. The digitized flow signal is then passed to the microprocessor's memory 62 for storage, for a predetermined time delay, prior to further processing. Referring to step 710, the tidal volume is extracted from the flow signal by integrating the flow signal data over time ($V_T = \int \dot{V} dt$). The resulting data is representative of the measured tidal volume and is passed to the microprocessor's memory 62 for storage prior to further processing.

Similarly, the pressure of the breathing proximate the pressure sensor 100 is sensed, preferably continually, and generates a pressure signal representative of that pressure which is transmitted toward the microprocessor 60 along line 113. If required, the pressure signal is then digitized by the second A/D converter 112 operating at an appropriate sampling frequency. The digitized pressure signal is then passed, for a predetermined time delay, to the microprocessor's memory 62 for storage prior to further processing.

In step 720, if desired, a real-time calculation of Crs and Rrs may be determined. Thence, in step 730, the average respiratory muscle pressure over a serial number of breaths ($Pmus_{avgN}(t)$), of the patient 10 is determined (hereinto referred to as the "average respiratory muscle pressure). A three step procedure is preferably utilized to determine $Pmus_{avgN}(t)$. First, using the equation of motion formula, where t is the time the pressure and flow rate are measured and/or sensed during an inspiration effort of the patient 10, the real-time respiratory muscle pressure is determined:

Pmus(t)=Pao(t)−[(Vao(t)/Crs)−($\dot{V}$ao(t)×Rrs)]−baseline pressure;

where:

Pmus(t): the real-time respiratory muscle pressure during inhalation;

Pao(t): the pressure of the breathing gas sensed derived from the pressure sensor 100;

Vao(t): the tidal volume of the breathing gas derived from the flow rate sensor 90;

V̇ao(t): the flow rate of the breathing gas derived from the flow rate sensor 90;

baseline pressure: the baseline pressure of the ventilator 20 (i. e., atmospheric pressure or the PEEP of the ventilator 20);

Crs: the predetermined static compliance of the respiratory system; and

Rrs: the predetermined resistance of the respiratory system.

Second, the average respiratory muscle pressure during the inspiratory period of a single breath is determined by averaging the determined real-time respiratory muscle pressure taken over the duration of the inspiratory period:

$$Pmus_{avg}(t) = \int_0^{Ti} (Pmus(t))\,dt;$$

where:

$Pmus_{avg}(t)$=the average respiratory muscle pressure during the inspiratory period of a single breath;

t=0 is the beginning of the inspiratory period by the patient 10 (the beginning of inspiration by the patient 10); and Ti=is the end of the inspiratory period of a single breath (the end of inspiration by the patient 10).

Finally, the average respiratory muscle pressure over a serial number of breaths is determined by averaging the determined $Pmus_{avg}(t)$ over the serial number of breaths:

$$Pmus_{avgN}(t) = 1\bigg/N\left[\sum_{breath=1}^{N} Pmus_{avg}(t)\right].$$

where:

$Pmus_{avgN}(t)$=the average respiratory muscle pressure of the patient 10 over a serial number of breaths; and N=the number of serial breaths.

The determined average respiratory muscle pressure ($Pmus_{avgN}(t)$) of the patient 10 is stored in the microprocessor's memory 62 for further processing.

The above equation of motion is well known to those skilled in the art. However, the use of the equation of motion to subsequently derive values of $Pmus_{avgN}(t)$ determined over a serial number of breaths and its correlation to the work of breathing of the patient 10 is not known. For enhanced accuracy, it is preferred that the average respiratory muscle pressure ($Pmus_{avgN}(t)$) of the patient be determined from any serial five breaths of the patient 10.

Figure 8A:
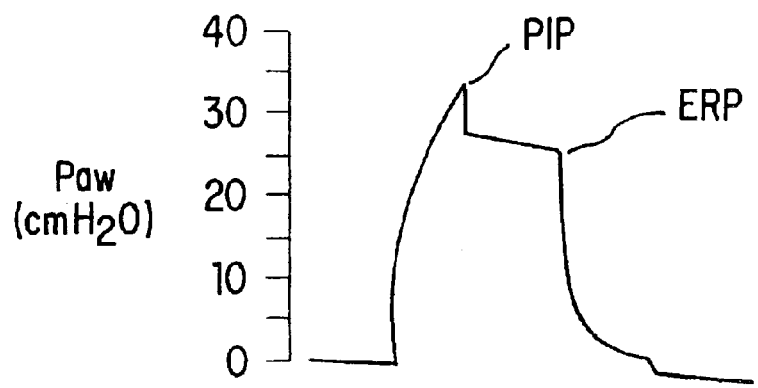
FIGS. 8A–C are graphical diagrams that illustrate the pressure of the gas at the airway opening (Pao) versus time; the flow rate of the gas (V) versus time; and the tidal volume of the gas ($V_T$) versus time during an end inspiratory pause determination of the compliance and resistance of the respiratory system.
Figure 8B:
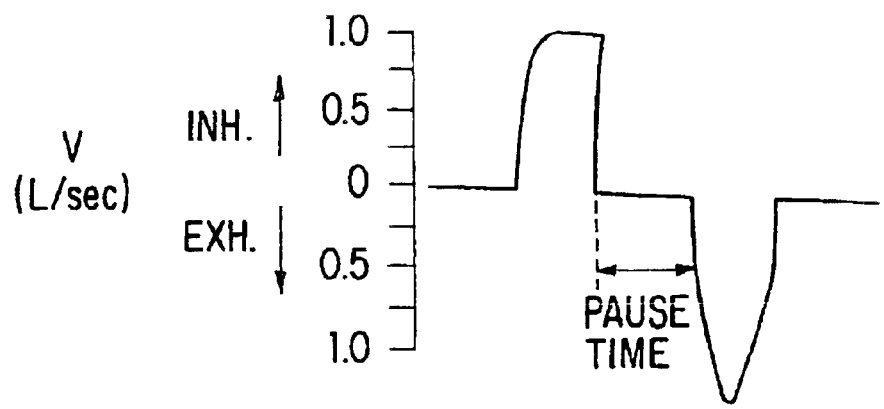
Figure 8C:
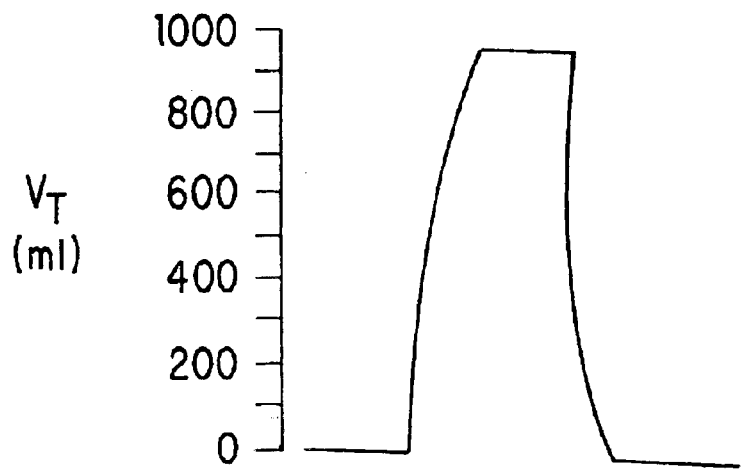
Figure 9:
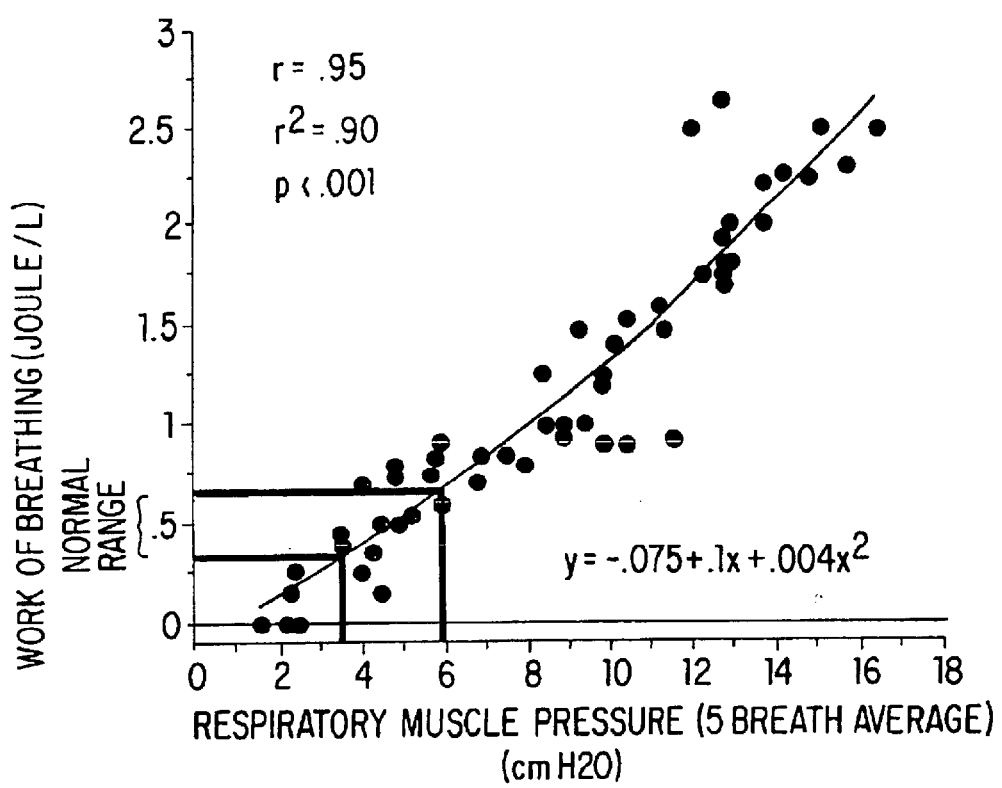
FIG. 9 is a work of breathing—average respiratory muscle pressure curve illustrating the correlation between the work of breathing of the patient and the average respiratory muscle pressure of the patient (averaged over a serial five breaths of the patient).

The constants for the compliance (Crs) and the resistance (Res) of a respiratory system for the above equation of motion are determined by methods well known in the art. The values for Crs and Rrs may be determined statically, i.e., prior to the initiation of the ventilation procedure using the ventilator 20 of the present invention, or on a real-time basis, i.e., immediately prior to the determination of the average respiratory muscle pressure in step 730. The preferred static method for determining Crs and Rrs of the respiratory system is known as the end-inspiratory pause methodology. Referring to FIGS. 8A–8C, prior to the initialization of the ventilator 20 in steps 400 and 600, the patient's spontaneous breathing is temporarily stopped by the injection of a muscle relaxant. The ventilator 20 then supplies breathing gas 32 to the patient 10 at a constant flow rate (V) and the pressure sensor 100 detects the peak inflation pressure (PIP) sensed at the airway opening Pao (i.e., the pressure of the breathing gas 32 proximate the pressure sensor 100), prior to the initiation of an inhalation hold. During the subsequent inhalation hold, no flow rate of breathing gas 32 is delivered to the patient 10 for a preselected period of, for example, 0.5 to 1.0 seconds. At the end of the inhalation hold, the pressure sensor 100 detects the plateau pressure (Pplat), indicative of the level of the static elastic recoil pressure, of the respiratory system. After the previously determined inhalation time period elapses, passive exhalation of the gas 32 is permitted. Further, the end inspiratory pressure, i.e. the baseline pressure, is detected by the pressure sensor 100. The tidal volume of the gas 32 is derived from the measured flow rates during the breathing cycle. The peak inhalation pressure, the plateau pressure, the end inspiratory pressure and the tidal volume of the breathing gas 32 may be stored in the microprocessor's memory 62 for further processing. The end-inspiratory pause procedure provides the following measurements:

V̇: the flow rate, in L/sec, of the breathing gas 32 during the breathing cycle;

$V_T$: the tidal volume, in L, of the exhaled breathing gas 32;

PIP: the peak inspiratory pressure, in cm H2O;

Pplat: the plateau pressure, in cm H2O of the respiratory system; and baseline pressure: the atmospheric pressure or the PEEP, in cm H2O.

The Crs and the Rrs of the respiratory system are then calculated using the formulas:

$$Crs = V_T/(P\text{plat}-\text{baseline pressure});$$

and $$Rrs = (PIP-P\text{plat})/\dot{V}.$$

Such static measurements of Crs and Rrs may be input into the microprocessor's memory 62 in steps 410 or 610 and the real-time measurement of Crs and Rrs in step 720 may then be bypassed.

Real-time measurement of the Crs and Rrs of the respiratory system is preferred over the static measurement of the Crs and Rrs of the respiratory system because the Crs and Rrs of the respiratory system may change during ventilatory support. Real-time methods for determining the Crs and Rrs, which may be implemented at step 720, allow for the determination of the Crs and Rrs "on the fly" which results in real-time computation and real-time values for the Crs and Rrs constants of the respiratory system. Some dynamic methods for determining Crs and Rrs include using the following formula for the computation of Crs:

$$Crs = V_T/PIP.$$

Here, Rrs in assumed as a constant value.

However, the preferred method for dynamically determining the Crs and Rrs of the respiratory system is to use a least-squares method which was first described by Wald et al. in the late 1960s. Resistance (Rrs) and Compliance (Crs) were computed based upon the measurement of patient airflow, volume and intraesophageal pressure (or airway pressure). Other researchers have applied this approach to more complicated models of the respiratory system that have included higher order terms and terms for inertance.

The least-squares fitting method assumes a specific model for the respiratory system, which is common in the respiratory mechanics literature (i.e., Stocks et al.), and fits the waveform data to that model. It is applied during the inspiration, expiration, and over the whole breath cycle. It uses all of the data points in the breath cycle and tends to be a more robust method than methods such as the Jonson or Suter methods for resistance which rely on the difference between two points in the breathing cycle and which are incorporated herein by reference. In the least-squares method, the lung is assumed to be a single compartment, the linear model mathematically expressed as:

$$Pi = (1/Crs)Vi + Rrs\dot{V}i$$

where

Rrs is the resistance of the respiratory system;

Crs is the compliance of the respiratory system;

Vi is the $i^{th}$ volume sample;

$\dot{V}i$ is the $i^{th}$ flow sample; and

Pi is the $i^{th}$ pressure difference (where the pressure difference is the pressure relative to a baseline level which may be either atmospheric pressure or PEEP).

The least-squares fitting method minimizes the summed squared errors between all of the observed pressure data points in the pressure wave form ($P_{OBSERVED}$) and a best fit pressure curve ($P_{BEST\ FIT}$). The least squares method minimizes the sum of squared errors (S) between $P_{OBSERVED}$ and $P_{BEST\ FIT}$:

$$S = \Sigma(P_{BEST\ FIT} - P_{OBSERVED})^2.$$

To "minimize" the error between the best fit and the observed pressures, the partial derivatives of S with respect to Rrs and Crs are computed, set to zero and solved for Rrs and Crs. This results in expressions for Rrs and Crs consisting of cross-products of volume and flow, pressure and volume and flow themselves.

$$Rrs = [(\Sigma V^2 \Sigma P\dot{V}) - (\Sigma PV \Sigma \dot{V}V)]/[(\Sigma V^2 \Sigma \dot{V}^2) - (\Sigma V\dot{V})^2];$$

and $$Crs = \Sigma V^2 / [\Sigma PV - (Rrs\Sigma V\dot{V})];$$

where

Rrs is the resistance of the respiratory system;

Crs is the compliance of the respiratory system;

V is the volume sample;

$\dot{V}$ is the flow sample; and

P is the pressure difference (where the pressure difference is the pressure sensed relative to a baseline level which may be either atmospheric pressure or PEEP, e.g, $P_{sensed}$-PEEP level).

The summations of these cross-products are accumulated throughout the inspiratory and expiratory portions of the breath from which the real-time compliance and resistance are calculated. Thus, these calculations, which are computationally intensive, are computed real-time throughout the breath cycle using running summations.

The determination of the compliance value is based upon the pressure, flow rate, and volume data samples sensed or measured by the pressure and flow rate sensors 100, 90 for a complete breath from the beginning of inspiration to the end of expiration. The inspiratory and expiratory resistance values are based upon based upon the pressure, flow rate, and volume data samples sensed or measured by the pressure and flow rate sensors 100, 90 for the inspiratory and expiratory portions of the cycle, respectively. Assuming that the determined Crs for the whole breath is the same during inspiration and exhalation, then $$Rrs = [(\Sigma PV - \Sigma V^2)/Crs]/\Sigma V\dot{V}.$$

Basically, the least-squares method of determining Crs involves sampling pressure-volume data points over an entire breath cycle and then minimized the sum of the square measurement errors between the observed pressure-volume curve and a best fit pressure-volume curve using standard statistical analysis well known in the art. Rrs is then determined based on the equation above. Real-time analysis of Crs and Rrs provides a simple method of measuring respiratory system compliance during mechanical ventilation, thereby obviating the need for sedation/paralysis and modification of the patient's breathing pattern required by the end-inspiratory pause methodology. Determining Crs and Rrs on a real-time basis provides the benefits of knowing the physiological condition, in terms of compliance and resistance, of the patient's respiratory system at the moment of calculation, and reducing the drug and manpower costs of repeating the end-inspiratory pause methodology several times a day.

Next, in step 740, the work of breathing of the patient 10 is determined. Through the discovery that there is a highly predictive relationship between the average respiratory muscle pressure ($Pmus_{avgN}(t)$) and the work of breathing of the patient 10 (WOB), the resultant current value of the patient's average respiratory muscle pressure may then be correlated to the work of breathing of the patient 10, as shown in step 740, by applying the following predictive relationship:

$$WOB = a + b(Pmus_{avgN}(t)) + c(Pmus_{avgN}(t))^2$$

where WOB is the work of breathing of the patient 10 in Joule/L, $Pmus_{avgN}(t)$ is the current value of the average respiratory muscle pressure of the patient 10 in cm H2O, and a, b, and c are constants dependent upon experimental data. The work of breathing of the patient 10 may then be recorded on a hard copy device such as a printer or may be visually displayed to the operator. The work of breathing of the patient 10 may also be stored in the memory 62 of the processor 60 for future use.

As mentioned above, the methodology of the preferred means for determining the work of breathing of the present invention results from the discovery that the average respiratory muscle pressure of the patient 10 presents a strong correlation to the work of breathing of the patient 10. This discovery resulted from statistical analysis of the correlation between the average respiratory muscle pressure of the patient 10 on one hand, and the work of breathing obtained through conventional methodologies.

Twenty-two adults were intubated and mechanically ventilated. The Crs and Rrs of the respiratory system were predetermined using the end-inspiratory pause procedure describe above. Data from a mainstream flow rate sensor, positioned between the proximal end 58 of the endotracheal tube 54 and the wye piece 48 of the ventilator conduit 40, and a pressure sensor 100 positioned near the wye piece 48 and the distal end 56 of the endotracheal tube 54, were directed to a processor 60 such as illustrated in FIG. 2, for determination of the average respiratory muscle pressure of the patient 10 simultaneously with the actual work of breathing of the patient 10.

To determine the actual work of breathing of the patient 10, a conventional work of breathing measurement technique known to those skilled in the art was used. A nasogastric tube with an incorporated esophageal balloon was inserted to measure intra esophageal pressure (Pes); correct position of the nasogastric tube was ascertained using the occlusion test. A second flow rate sensor was positioned in series between the endotracheal tube 54 and the wye piece 48 to measure the volume of the gas 32 at the proximal end 58 of the endotracheal tube 54 (Vao). Pes and Vao were directed to a respiratory monitor, a Bicore monitor, that provided real time measurement of the patient's total actual work of breathing using the Campbell diagram and commercially available Campbell diagram software (which plotted the change in volume plotted over Pes during spontaneous inhalation and exhalation of the patient 10, determined the flow resistive work of breathing and the elastic work of breathing of the patient 10, and summed the determined flow resistive work of breathing and the elastic work of breathing to compute the total actual work of breathing of the patient 10).

The following data were developed for each set of measurements:

Pao(t): the pressure sensed proximate the pressure sensor;
Vao(t): the tidal volume of the breathing gas 32 derived from the flow rate sensor;
$\dot{V}ao(t)$: the flow rate of the breathing gas 32 proximate the flow rate sensor;
baseline pressure: the baseline pressure of the ventilator 20 (i.e., atmospheric pressure or the PEEP of the ventilator 20);
WOB: the actual total work of breathing of the patient 10;
Pmus(t), from:

$$Pmus(t) = Pao(t) - [(Vao(t)/Crs) - (\dot{V}ao(t) \times Rrs)] - \text{baseline pressure};$$

$Pmus_{avg}(t)$, from:

$$Pmus_{avg}(t) = \int_0^{Ti} (Pmus(t))\, dt;$$

where t=0 at the beginning of inspiration and t=$T_i$ at the end of inspiration; and
$Pmus_{avg5}(t)$, from:

$$Pmus_{avg5}(t) = 1 \Big/ 5 \left[ \sum_{breath=1}^{5} Pmus_{avg}(t) \right]$$

where $Pmus_{avg5}(t)$ is the average respiratory muscle pressure over five serial breaths of the patient 10.

The results of a correlation analysis of $Pmus_{avg5}(t)$ and WOB for each of the measured sets of data showed a positive and significant correlation between $Pmus_{avg5}(t)$ and WOB. The regression analysis fields the following predictive polynomial relationship:

$$WOB = a + b(Pmus_{avg5}(t)) + c(Pmus_{avg5}(t))^2$$

where WOB is the work of breathing of the patient 10 in J/min, $Pmus_{avgN}(t)$ is the current value of the average respiratory muscle pressure of the patient 10 measured over a serial five breath time period, and a, b, and c are constants, the value of which depends upon the experimental data. For example, referring to the experimental plot illustrated in FIG. 10, the experimental data points representative of the twenty-two measurements taken on the patients 10, using the average respiratory muscle pressure derived from a serial five breath average are shown against an x-axis representative of average respiratory muscle pressure $Pmus_{avg5}(t)$ (cm H2O) and a y-axis representative of the WOB simultaneously derived using the conventional methodology described above. Statistical analysis yielded curve having the constant values for the predictive relationship of:

a=−0.075;
b=0.1; and
c=0.004.

Figure 10:
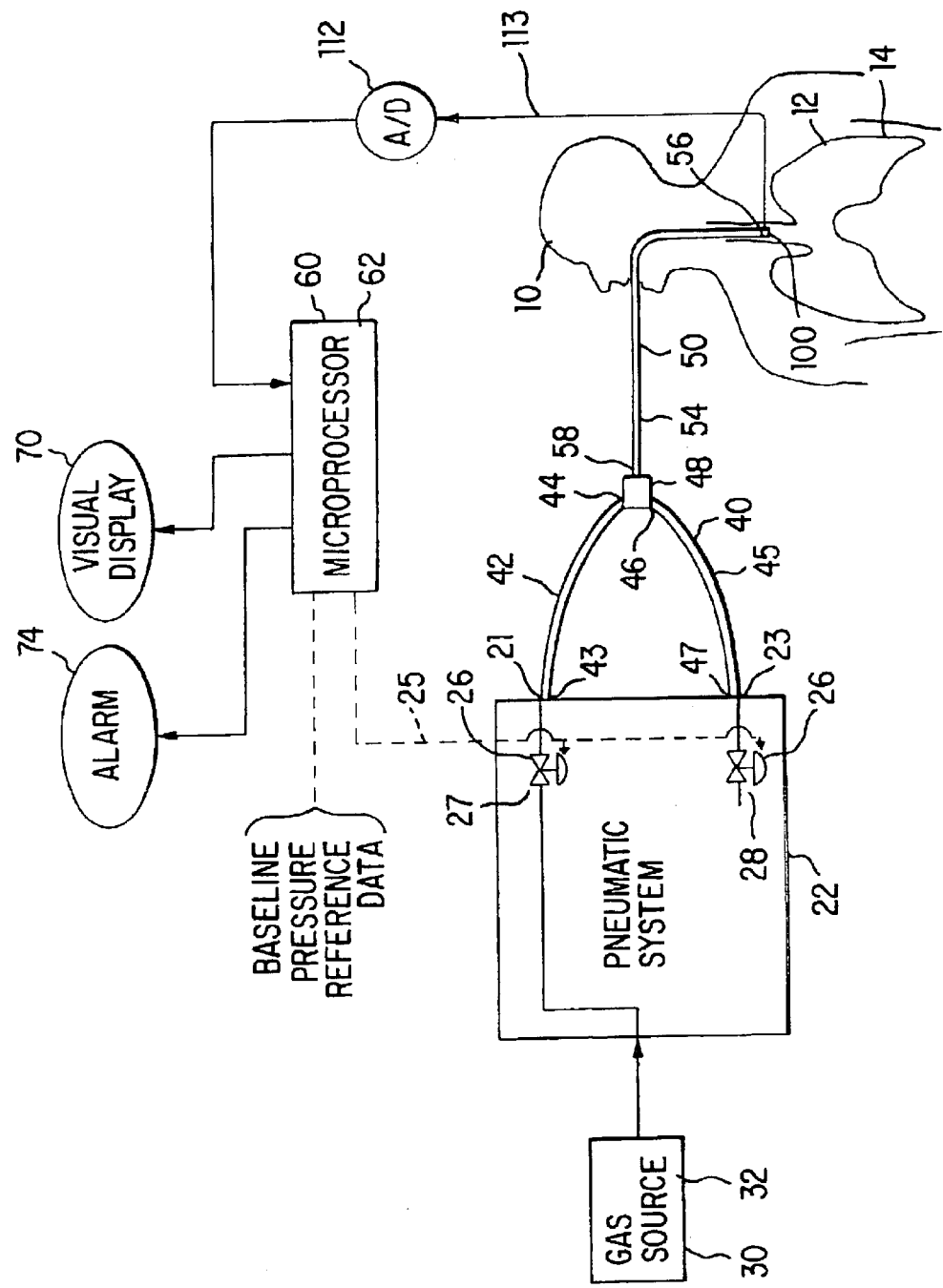
FIG. 10 is a block diagram of the medical ventilator according to the second embodiment of the present invention showing the pressure sensor near the distal end of the endotracheal tube.

Still referring to FIG. 10, the positive and significant correlation between Pmus and WOB of the patient 10 (r=0.95) indicates that the current value of average respiratory muscle pressure $Pmus_{avgN}(t)$ from the sensed flow rate and pressure of the breathing gas 32 is a good predictor of the work of breathing of the patient 10 ($r^2$=0.90).

It must be emphasized that the above equations are merely exemplary and represent the best correlations/predictions obtained by regression analysis, using an alpha set at 0.05 for statistical significance, on a limited set of patients 10 thus providing only a limited set of measurements. The measurements were made under clinical conditions and no attempt was made to select the best data or to determine the reason for readings that departed significantly from the average value. In addition to obtaining larger and more carefully controlled data samples, it is probable that the predictive equation could be further improved by using more sophisticated analysis.

The above results demonstrate, however, that the determination of the average respiratory muscle pressure of the patient 10 may provide a simple and easy method for predicting the measured level of the work of breathing of the patient 10.

Tracheal Pressure Ventilator Control

FIG. 10 shows a second embodiment of a medical ventilator 20 of the present invention. The construction of the second embodiment is similar to the first embodiment and, accordingly, use the same reference numbers for similar components. The components in FIG. 10 that use the same reference numbers as in FIGS. 1–2 are substantially equivalent and, therefore, the description thereof is omitted for the second embodiment.

During spontaneous or assisted ventilation, the patient 10 is required to "work" (to varying degrees) by using the respiratory muscles in order to breath. This work of breathing of a patient 10 breathing spontaneously during ventilatory support by a medical ventilator 20 may be divided into two components: first, the imposed work of breathing of the breathing apparatus; and second, the physiologic work of breathing of the patient 10. The imposed work of breathing is the resistive work of breathing imposed by the breathing apparatus (the physical construct of the entire ventilation support external to the patient' lungs 14, i.e., the endotracheal tube 54, the ventilator conduit 40, the medical ventilator 20, etc.) upon the spontaneously breathing patient 10 receiving ventilator support. The physiologic work of breathing of the patient 10 consists of two components: first, the resistive work of breathing of the airways of the patient 10, and two, the elastic work of breathing of the lungs 14 and the chest wall. It is desirable to reduce or, even more desirable, to nullify the imposed work of breathing as the patient 10 may be detrimentally affected by an excessively high expenditure of energy early in the inspiration process caused by the respiratory muscle force required to overcome the imposed work of breathing of the breathing apparatus. Patient's may fatigue under the imposed work of breathing workload which predisposes the patient 10 to respiratory muscle fatigue, respiratory distress, respiratory or ventilator dependancy, and/or failure. Nullification of the imposed work of breathing also allows for the contemporaneous determination of the physiologic work of breathing.

Conventional methods and apparatus for reducing or minimizing the imposed work of breathing are inadequate. Typically, these conventional efforts rely upon a means of "triggering" the ventilator 20 to supply inspiratory ventilation support upon the sensing of an inspiration effort. The conventional means for triggering the ventilator 20 may be classified as either pressure or flow-by triggering. In conventional pressure triggering, the withdrawal of the small volume of gas 32 that occurs as a breath is initiated by the patient 10 results in a corresponding drop in pressure which is monitored via a pressure sensor that is typically disposed within the ventilator conduit 40 at or near the wye piece 48 or within either the inhalation conduit 42 or the exhalation conduit 45. At the onset of spontaneous inhalation by the patient 10, the pressure change is detected at the pressure sensor which functions to trigger the ventilator 20 "ON" to then actively inflate the lungs 14 of the patient 10 during ventilation support. Several disadvantages are associated with the use of conventional pressure triggering to reduce the imposed work of breathing. First, the chosen pressure measurement sites produce a pressure signal that measures the pressure of the breathing gas 32 proximate the pressure sensor which is remote from the actual intratracheal pressure drop occurring within the patient's trachea during initiation of the spontaneous inhalation effort. The pressure drop sensed by the pressure sensor is then used as a basis for regulating or controlling the amount of pressure or flow rate (to generate the requisite pressure) of breathing gas 32 applied to the lungs 14. Because the chosen sites are so remote from the lungs 14 of the patient 10, the resulting pressure measurements are an inherently inaccurate measurement of the pressure on the airways and lungs 14 of the patient 10 which causes a marked increase in the effort or work to inhale by the patient 10 as the regulated amount of breathing gas 32 applied to the patient 10 is calculated in error due to the "approximated" value of the pressure drop sensed.

Second, and once again because of the remote pressure sensing measurement sites, in conventional pressure triggering there is a significant amount of lag time and associated negative pressure that always occurs between the onset of the patient's inspiratory effort and the time that the gas pressure or flow reaches the patient's airway. This lag time is generally referred to as a ventilator's response time, and commonly occupies a small by significant portion of a patient's total inspiration time. The pressure waves that are indicative of the pressure drop travel to the pressure sensor at the speed of sound in the breathing gas 32, which is approximately 1 millisecond per foot. Due to factors inherent in conventional ventilator design and the prior art locations of the pressure sensing site, the resulting patient inspiration effort can typically continue for as long as 40 to 500 milliseconds without ventilator assistance. Thus, under the conventional pressure drop triggering schemes, the pressure drop, which a patient 10 is required to create in order to trigger a breath in a closed breathing circuit, can require a significant expenditure of energy by the patient 10. This imposed work of breathing on the patient 10 can be detrimental in that respiratory muscles already loaded and nearly fatigued by an operation or other patient conditions may continue to fatigue, which, if this process continues, may result in the failure or severe compromise of the ventilation support procedure. Additionally, the forced respiratory work required to trigger ventilation may be beyond the capacity of infants, small children, or patients' suffering from trauma or disease.

In flow-by triggering, the signal to cycle "ON" the ventilator 20 to deliver pressure or flow support of a patient's inhalation effort is determined by monitoring the flow in the patient's ventilator conduit 40 or inside the ventilator 20. In such a system, a single flow rate sensor is typically positioned inside the ventilator 20 to monitor the flow of gas 32 that a patient 10 withdraws from the ventilator 20 via the ventilator conduit 40 and triggers a pressure or flow based breath support when the patient's inspiratory flow equals a certain level. However, such a closed system flow based trigger is not an improvement over a conventional pressure triggering system, because all of the same delays and work required of the patient 10 (i.e., imposed on the patient 10) are still present. In addition, a significant negative pressure drop is still required to start the breath and there is no continuous flow to support the earliest phase of the breath. Significantly, even if there were some form of continuous flow to support the earliest phase of the breath in an effort to minimize the imposed work of breathing required of the patient 10 to cause the requisite negative pressure drop, the remote location of the flow rate sensor would still cause inappropriate application of the pressure or flow based breath support due to the inherent inadequacy of the measurement site. Therefore, in conventional triggering means developed to minimize the imposed work of breathing of the patient 10, the patient 10 must still overcome the substantial resistance and inertia of the breath triggering process. The second embodiment of the present invention overcomes the prior art limitations, and due to the diminimus response time, aids in reducing and effectively nullifying the imposed work of breathing of the patient 10.

Referring now to FIG. 10, the second embodiment of the present invention is shown. The second embodiment of the present invention is directed to the tracheal pressure ventilation control of a medical ventilator 20 for supplying a breathing gas 32 for use in a medical procedure, such as ventilation support. The breathing gas 32 is received into the medical ventilator 20 from a gas source 30 of one or more breathing gases 32 and the gas 32 exits the ventilator 20 in flow communication with a functionally open ventilator conduit 40. The ventilator conduit 40 has a patient breathing attachment 50, preferably an endotracheal tube 54, in fluid communication with the interior, i.e., the lungs 14 and airways, of the patient 10.

The pressure sensing means is disposed within the flow path of the gas 32 within the endotracheal tube 54. More particularly, in this embodiment, the pressure sensing means is preferably disposed near or proximate the distal end 56 of the endotracheal tube 54. The pressure sensing means may be the means described above in the first embodiment above. However, it is preferred that the pressure is sensed using a catheter, well known to one skilled in the art, inserted within the endotracheal tube 54 [not shown]. The catheter has a distal end that is proximate the distal end 56 of the endotracheal tube 54. It is more particularly preferred that the pressure sensing means be a pressure sensor 100, such as a piezoresistive pressure sensor, embedded in the inner sidewall of the endotracheal tube 54 proximate the distal end 56 of the endotracheal tube 54 [not shown]. The pressure sensor 100 is in communication with the flow of gas 32 within the endotracheal tube 54. For example, the preferred pressure sensor 100 may be comprised of a disposable endotracheal tube provided by Mallinckrodt Critical Care having a pressure sensor 100 embedded within a lumen in the sidewall of the endotracheal tube 54 near the distal end 56 of the endotracheal tube 54.

This position of the pressure sensor 100 allows the ventilator 20 to respond faster to breathing gas pressure changes and to provide a more accurate sensing of the breathing gas pressure within the lower end of a patient's trachea proximate the alveoli of the lungs 14 of the patient 10. Therefore the ventilator 20, due to the virtual elimination of the lag time inherent in the transmittal of the requisite pressure waves and the resulting minimal ventilator response time and the more accurate pressure measurement of the actual pressure within the patient's lungs 14 resulting from the measurement of the gas pressure at the preferred distal end 56 of the endotracheal tube 54, may respond quickly and accurately to breathing gas pressure changes which nullifies the imposed work of breathing of the breathing apparatus.

The monitoring means, such as a processor 60 or the preferred microprocessor 60, is connected to the pressure sensing means to monitor the pressure of the gas 32 proximate the pressure sensing means and is responsive to the output of the pressure sensing means. The monitoring means compares the output of the pressure sensing means to a predetermined baseline pressure, which is inputted by the operating clinician and stored in memory 62, and, if it is determined that the pressure of the gas 32 proximate the pressure sensing means is below the predetermined baseline pressure, generates a pressure response signal based on the determination. However, if the monitoring means determines that the pressure of the gas 32 proximate the pressure sensing means exceeds the predetermined baseline pressure, the monitoring means generates a termination signal thereof.

As one skilled in the art will appreciate, the regulating means of the ventilator 20, electrically coupled to the gas delivery means, may be responsive to the monitoring means to regulate the pressure and/or flow rate of the breathing gas 32 provided to the patient 10 so that the pressure of the breathing gas 32 near the distal end 56 of the endotracheal tube 54 is maintained at the predetermined baseline pressure. The regulating means, in response to the pressure response signal, adjusts at least one of the actuators 26 of the gas delivery means, as necessary, to increase the pressure and/or flow rate of the breathing gas 32 delivered by the ventilator 20 so that the pressure of the gas 32 proximate the distal end 56 of the endotracheal tube 54 is maintained at the predetermined baseline pressure. Similarly, the regulating means, in response to the termination signal, adjusts at least one of the actuators 26 of the gas delivery means, as necessary, to decrease the pressure and/or flow rate of the breathing gas 32 delivered by the ventilator 20 so that the pressure of the gas 32 proximate the distal end 56 of the endotracheal tube 54 is maintained at the predetermined baseline pressure. Thus, the regulating means, which is responsive to the pressure response signal and the termination signal of the monitoring means, adjusts at least one of the actuators 26 of the pneumatic system 22 of the ventilator 20 so that the output pressure of the breathing gas 32 exiting from the distal end 56 of the endotracheal tube 54 is maintained at the predetermined baseline pressure. Preferably, the regulating means is automatically and proportionally controlled in response to the monitoring means so that the pressure of the breathing gas 32 proximate the distal end 56 of the endotracheal tube 54 is maintained at the predetermined baseline pressure.

Because of the ability of the medical ventilator 20 of the second embodiment of the present invention to precisely control the pressure of the breathing gas 32 proximate the distal end 56 of the endotracheal tube 54 and to thereby nullify the imposed work of breathing, the use of the tracheal pressure ventilation control embodiment need not be restricted to present ventilatory support techniques. In fact, it is expected that the ventilator 20 of the second embodiment of the present invention will assist physicians to develop completely new ventilatory support techniques.

In an effort to reduce both the patient's work of breathing to sustain a breath and to minimize the imposed work of breathing required by the patient 10 to trigger the ventilator 20 (it is desirable to reduce the effort expended in both of these phases as a high level of work or effort by the patient 10 can cause further damage to a weakened patient 10 or be beyond the capabilities of small or disabled patients 10), it is further anticipated and, indeed, expected that the second embodiment of the present invention would be used concurrently with any spontaneous or assisted mode of ventilator support know in the art that the clinician desires to use to reduce the patient's work of breathing to sustain a breath. Thus, the first embodiment of the ventilator 20 may be used concurrently with the tracheal pressure ventilation control of the second embodiment of ventilator 20. While both the first embodiment and the second embodiment discussed herein are separately helpful in reducing the work to be performed by the patient 10 on the ventilator 20, it would be desirable to provide a ventilator 20, or ventilator system, that combined the work of breathing reduction concepts inherent in the first and second embodiments, to thereby enable the ventilator 20 to manage all phases of the energy expended by the patient 10. Such a level of performance is unavailable in current ventilators.

As discussed above in the first embodiment, the work of breathing of the patient 10 is monitored and the pressure support ventilation level that will maintain the patient's work of breathing within a predetermined work of breathing range is determined and either the pressure support ventilation level is set by the operating clinician, in the open-loop operation, or the pressure support ventilation level is controlled and set automatically by the ventilator 20 without operator required intervention, in the closed-loop operation. By setting the advised level of pressure support ventilation, the ventilator 20 improves the patient's efforts to breath by reducing the work to sustain a breath to the level of work desired by the clinician. In effect, the patient's work of breathing to sustain a breath is reduced because the appropriate quality and quantity of ventilation support is supplied to the patient 10 based on the patient's current pathophysiology. In the second embodiment, however, the pressure of the breathing gas 32 proximate the distal end 56 of the endotracheal tube 54 is monitored and controlled in real time to a defined set point to nullify the imposed work of breathing. The pressure sensor 100 is used as a pressure feedback loop that will modulate the pressure or the total flow rate of the breathing gas 32 supplied by the ventilator 20 to maintain the pressure of the breathing gas 32 exiting the distal end 56 of the endotracheal tube 54 at the predetermined baseline pressure.

As will be noted, many components of the second embodiment are similar to those for the first embodiment with the significant differences being the pressure sensor 100 is disposed proximate the distal end 56 of the endotracheal tube 54 and the flow rate sensor 90 is not required. If, however, the first embodiment of the ventilator 20 is used simultaneously with the second embodiment, the only significant difference, as would be apparent to one skilled in the art, is that the pressure sensor 100 of the first embodiment must be disposed proximate the distal end 56 of the endotracheal tube 54.

If desired, the work of breathing of the patient 10 may be determined by any means known in the art such as the means described above in the first embodiment. However, when the second embodiment of the ventilator 20 is used, the work of breathing determined will be the physiologic work of breathing of the patient 10 as the imposed work of breathing would have been nullified by the ventilator 20. As one skilled in the art would appreciate, by nullifying the imposed work of breathing and allowing the measurement of the physiologic work of breathing of the patient 10, the simultaneous use of the second embodiment of the ventilator 20 with the first embodiment of the ventilator 20 allows the operator to maintain the level of pressure support ventilation that will maintain the physiologic work of breathing of the patient 10 within the predetermined work of breathing range. The combination of the first embodiment of the ventilator 20 and the tracheal pressure ventilation control of the second embodiment of the ventilator 20 described herein for concurrent operation thus yields a ventilator 20 with an enhanced ability to minimize the work of breathing of the patient 10 in all phases of the ventilatory support cycle, with the corresponding therapeutic effects upon the patient 10, by more accurately responding to the patient's actual pathophysiology to beneficially reduce both the work required to sustain a breath and the work required to trigger the ventilator support selected. As one skilled in the arts would appreciate, a ventilator would be enhanced, and the overall work of breathing of the patient 10 reduced, through the concurrent use of the second embodiment of the present invention, tracheal pressure ventilation control, and any other pressure support mode selected by the clinician for spontaneous or assisted ventilation of the patient 10.

Figure 11:
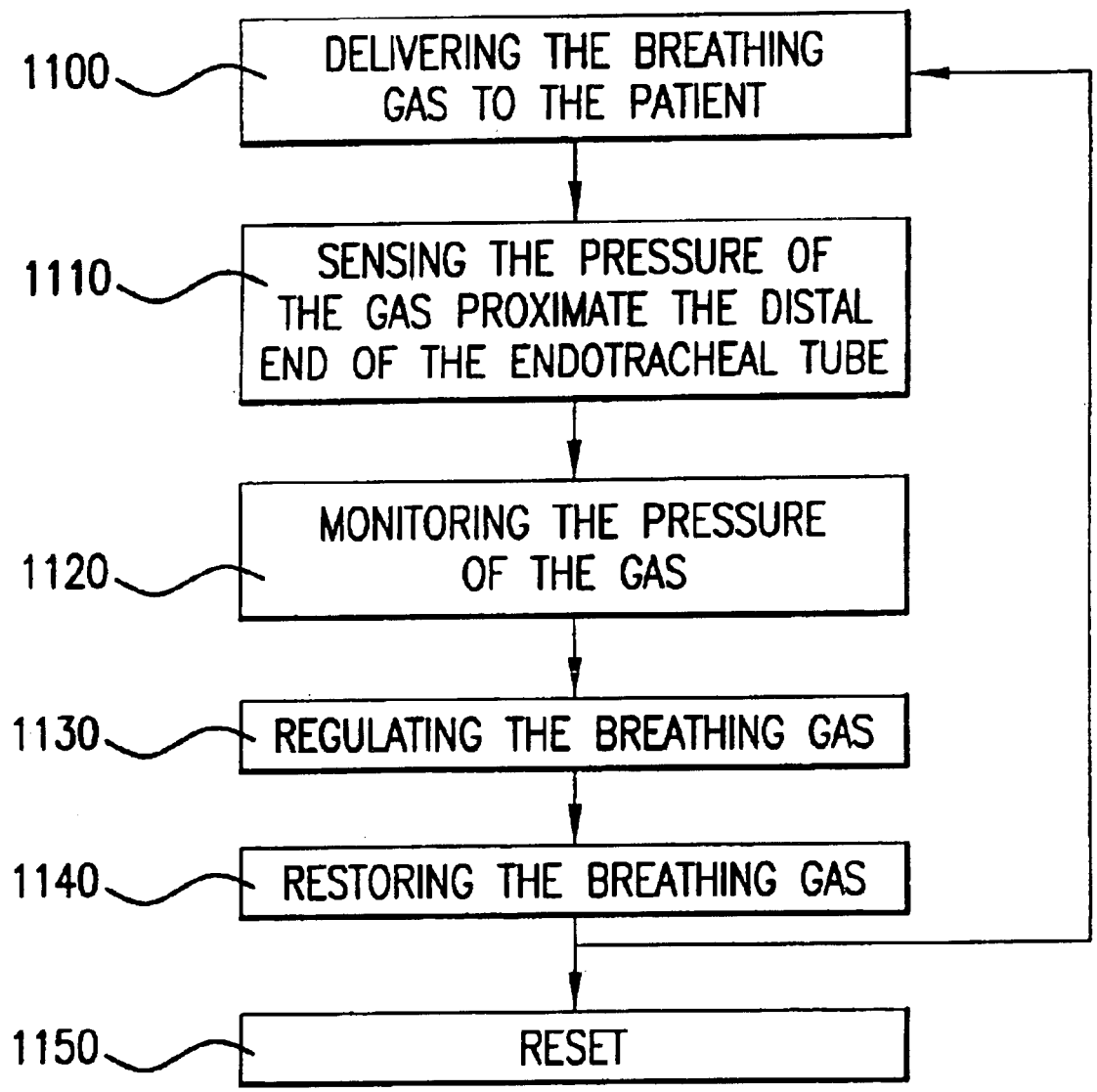
FIG. 11 is a flow chart illustrating a general sequence of steps for carrying out the tracheal pressure ventilator control embodiment of the present invention.

Referring now to FIG. 11, the second embodiment of the ventilator 20 relates to a method of controlling, for any selected period of time, the ventilator 20 for nullifying the imposed work of breathing during the ventilation of a patient 10 supplied with a breathing gas 32 from the medical ventilator 20, the gas 32 being pressure and/or flow rate controlled by the ventilator 20, comprising the steps of: delivering the breathing gas 32 from the ventilator 20 into the endotracheal tube 54 and thence into fluid communication with the lungs 14 of the patient 10 in step 1100; sensing the pressure of the breathing gas 32 within the endotracheal tube 54, particularly sensing the pressure of the breathing gas 32 in the flow path of the breathing gas 32 within the endotracheal tube 54 proximate the distal end 56 of the endotracheal tube 54 in step 1110; monitoring the pressure of the breathing gas 32 from the sensed pressure to determine when the pressure of the breathing gas 32 proximate the distal end 56 of the endotracheal tube 54 deviates from a predetermined baseline pressure in step 1120; regulating the breathing gas 32 supplied by the medical ventilator 20 when it is determined that the pressure of the breathing gas 32 proximate the distal end 56 of the endotracheal tube 54 is less than the predetermined baseline pressure, preferably by controlling the ventilator 20 to increase the pressure and/or flow rate of the breathing gas 32 supplied by the ventilator 20 in step 1130; and restoring the breathing gas 32 supplied by the ventilator 20 to the predetermined baseline pressure prior to the next inhalation effort of the patient 10, preferably by controlling the ventilator 20 to decrease the pressure and/or flow rate of the breathing gas 32 supplied by the ventilator 20 when it is determined that the pressure of the breathing gas 32 proximate the distal end 56 of the endotracheal tube 54 is greater than the predetermined baseline pressure in step 1140. Preferably, the steps of regulating and restoring the ventilator 20 are automatically and proportionally controlled so that the pressure of the breathing gas 32 proximate the distal end 56 of the endotracheal tube 54 is maintained at the predetermined baseline pressure. The ventilator 20 continues to execute until reset in step 1150. The ventilator method may also include the step of inputting a predetermined baseline pressure prior to the step of delivering the gas 32.

The method may also include the further step of determining the patient physiologic work of breathing. As noted above, this may be done by any method known in the art. However, if the surrogate method of determining the work of breathing of the patient 10 described in the first embodiment above is used, the method requires the steps of sensing the flow rate of the breathing gas 32 in the ventilator conduit 40 and of determining the patient physiologic work of breathing from the sensed pressure and the sensed flow rate of the breathing gas 32 by the steps described in the first embodiment above.

Figure 12:
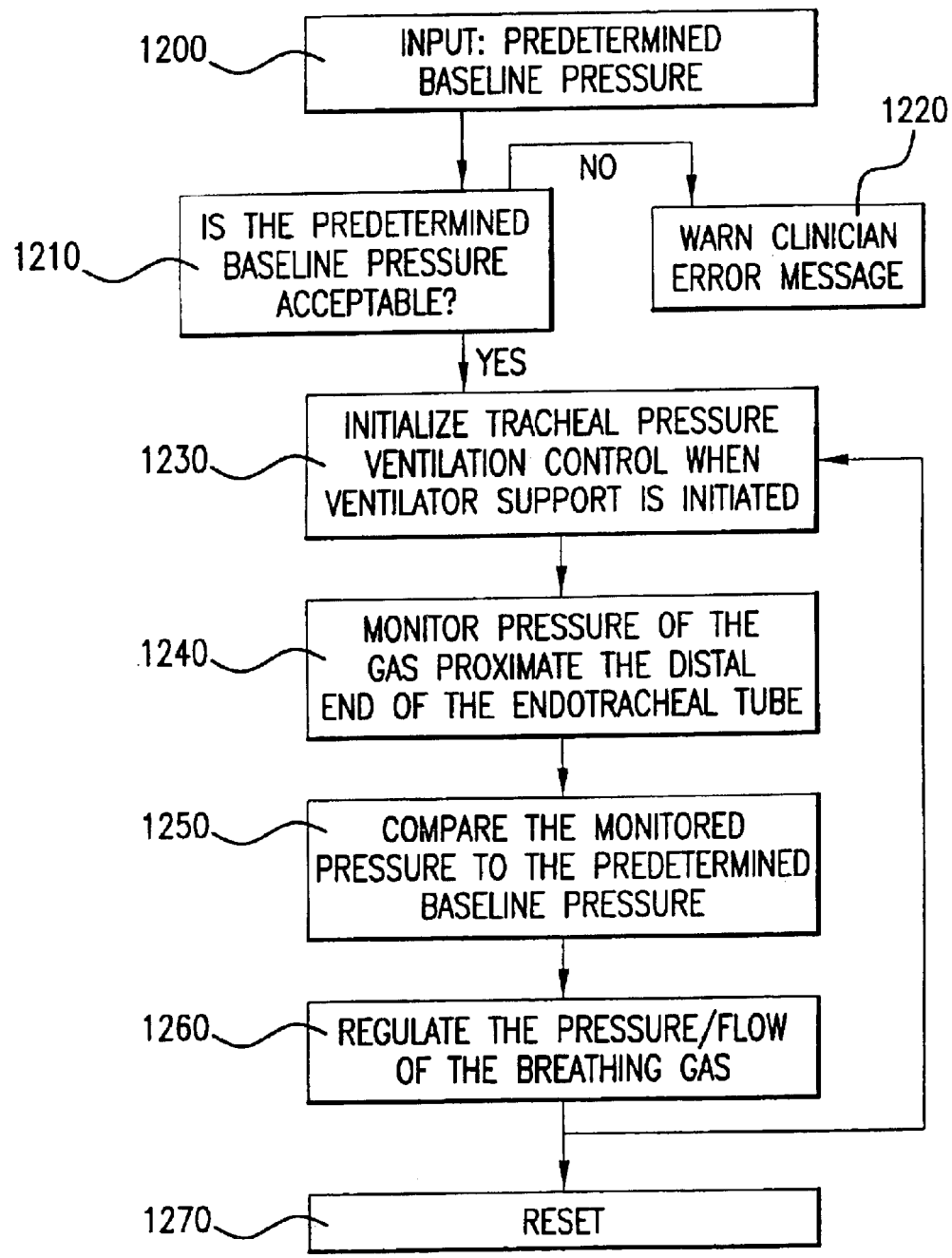
FIG. 12 is a flow chart illustrating a preferred sequence of steps for carrying out the tracheal pressure ventilator control embodiment of the present invention as executed by a programmable microprocessor.

Referring now to FIG. 12, a general flowchart for the second embodiment of the present invention is illustrated. The flow chart shows a "while" loop that may be used singularly or in combination with any type of ventilatory support technique to nullify the imposed work of breathing. The "while" loop continues to execute as long as the ventilator 20 is not reset. At Block 1200, the predetermined baseline pressure is selected. At Block 1210, the selected predetermined baseline pressure may be checked to verify their physiological acceptability. If the baseline pressure is not acceptable, Block 1220 sends an error message that is displayed via the alarm means and/or the display means to warn the clinician of the problem. If the baseline pressure is acceptable, then the tracheal pressure ventilation control is initialized when ventilator support is provided to the patient 10 at Block 1230. At Block 1240, the pressure of the gas 32 proximate the distal end 56 of the endotracheal tube 54 is monitored. At Block 1250, it is determined if the pressure of the gas 32 proximate the distal end 56 of the endotracheal tube 54 is greater than or less than the predetermined baseline pressure and the magnitude of the pressure deviation from the predetermined baseline pressure is determined. Then, at Block 1260, the control algorithms of the ventilator 20 automatically and proportionally tries to maintain the pressure proximate the distal end 56 of the endotracheal tube 54 at the predetermined baseline pressure. The program continues to operate until it is reset at Block 1270.

Although the present invention has been described with reference to specific details of certain embodiments thereof, it is not intended that such details should be regarded as limitations upon the scope of the invention except as and to the extent that they are included in the accompanying claims.

What is claimed is:

1. A method of controlling a medical ventilator on demand during the ventilation of a patient for nullifying the imposed work of breathing during an inhalation effort by the patient, the medical ventilator in fluid communication with a source of breathing gas and with a functionally open gas ventilator flow conduit having an endotracheal tube in fluid communication with the patient, the endotracheal tube having a distal end which is adapted for disposition in the patient's trachea, the method comprising the steps of:

a) selecting a predetermined baseline pressure that is at least zero;

b) delivering a predetermined supply of the breathing gas from the ventilator based on a preselected ventilation mode into the endotracheal tube and thence into the patient at the initiation of the inhalation effort;

c) sensing the pressure of the breathing gas proximate the distal end of the endotracheal tube;

d) monitoring the pressure of the breathing gas;

e) automatically and proportionally controlling the supply of breathing gas delivered by the ventilator to substantially maintain the pressure of the breathing gas proximate the distal end of the endotracheal tube at the predetermined baseline pressure throughout the inhalation effort.

2. The method of claim 1, wherein the step of monitoring comprises determining when the pressure of the breathing gas proximate the distal end of the endotracheal tube drops below the value of the predetermined baseline pressure.

3. The method of claim 2, wherein the step of controlling comprises regulating the supply of breathing gas delivered by the medical ventilator when it is determined that the pressure of the breathing gas proximate the distal end of the endotracheal tube is less than the predetermined baseline pressure.

4. The method of claim 3, wherein the step of controlling further comprises restoring the breathing gas supplied by the medical ventilator to the predetermined baseline pressure prior to the next inhalation effort of the patient.

5. The method of claim 3, wherein the regulating step comprises controlling the medical ventilator so as to increase the supply of the breathing gas delivered by the medical ventilator when it is determined that the pressure of the breathing gas proximate the distal end of the endotracheal tube is less than the predetermined baseline pressure so that the pressure of the breathing gas proximate the distal end of the endotracheal tube is maintained at the predetermined baseline pressure.

6. The method of claim 4, wherein the restoring step comprises the step of controlling the medical ventilator so as to decrease the supply of the breathing gas delivered by the ventilator when it is determined that the pressure of the breathing gas proximate the distal end of the endotracheal tube is greater than the predetermined baseline pressure.

7. The method of claim 1, wherein the step of sensing the pressure of the breathing gas is performed in a flow path of the gas within the endotracheal tube.

8. The method of claim 1, further comprising the step of determining a patient physiologic work of breathing.

9. The method of claim 8, wherein the step of determining a patient physiologic work of breathing comprises the steps of:
  a) sensing the volume of the breathing gas in the ventilator flow conduit; and
  b) determining the patient physiologic work of breathing from the sensed pressure and the sensed volume of the breathing gas in the ventilator flow conduit.

10. The method of claim 8, further comprising the step of displaying the patient physiologic work of breathing.

11. The method of claim 9, wherein the step of sensing the volume of the gas is performed in a flow path of the gas within the ventilator conduit.

12. A medical ventilator for providing breath support to a patient during a medical procedure, the medical ventilator suitable for connection to a source of one or more breathing gases, and to a ventilator flow conduit having an endotracheal tube, the endotracheal tube having a distal end adapted for positioning within the patient's trachea, the medical ventilator comprising:
  a) a pressure sensor disposed in a flow path of the breathing gas within the endotracheal tube which measures the pressure of the gas proximate the pressure sensor and which provides a pressure signal representative thereof, wherein the pressure sensor is located proximate the distal end of the endotracheal tube;
  b) a processor having a program for delivering a supply of the breathing gas from the ventilator based on a preselected ventilation mode at the initiation of an inhalation effort by the patient, the processor responsive to the gas pressure signal generated by the pressure sensor and having a program for automatically and proportionally controlling a supply of the breathing gas delivered thereto the endotracheal tube to substantially maintain the pressure of the breathing gas proximate the distal end of the endotracheal tube at a predetermined baseline pressure that is at least zero throughout the inhalation effort of the patient so that imposed work of breathing is nullified during the inhalation effort; and
  c) at least one actuator, responsive to the processor, to regulate the supply of the breathing gas provided by the ventilator to the patient.

13. The medical ventilator of claim 12, wherein the processor detects when the pressure of the gas within the endotracheal tube drops below the predetermined baseline pressure and generates a response signal thereof.

14. The medical ventilator of claim 13, wherein the actuator is responsive to the response signal to increase the supply of the breathing gas provided by the medical ventilator so that the pressure of the breathing gas proximate the distal end of the endotracheal tube is maintained at the predetermined baseline pressure.

15. The medical ventilator of claim 13, wherein the processor detects when the pressure of the breathing gas within the endotracheal tube exceeds the predetermined baseline pressure and generates a termination signal thereof.

16. The medical ventilator of claim 15, wherein the actuator is responsive to the termination signal to decrease the supply of the breathing gas provided by the ventilator so that the pressure of the breathing gas at the distal end of the endotracheal tube is maintained at the predetermined baseline pressure.

17. The medical ventilator of claim 12, wherein the actuator regulates a pressure, a flow rate, or a combination of both to regulate the supply of the breathing gas provided by the ventilator to the patient.

18. The medical ventilator of claim 12, wherein the pressure sensor comprises an analog pressure sensor.

19. The medical ventilator of claim 18, further comprises a digitizer which receives the pressure signal from the analog pressure sensor and converts the pressure signal into a digitized pressure signal which is received by the processor.

20. A medical ventilator for nullifying the imposed work of breathing during an inhalation effort of a patient, the medical ventilator in fluid communication with a source of breathing gas and with a functionally open gas ventilator flow conduit having an endotracheal tube, the endotracheal tube having a distal end adapted for disposition within the patient's trachea, the medical ventilator comprising:
  a) pressure sensing means disposed within the endotracheal tube for sensing the pressure of the gas proximate the distal end of the endotracheal tube;
  b) monitoring means connected to the pressure sensing means for monitoring the pressure of the gas proximate the distal end of the endotracheal tube;
  c) gas delivery means for providing a supply of breathing gas to the ventilator flow conduit; and
  d) a regulating means electrically connected to the monitoring means and the gas delivery means, the regulating means delivering a predetermined supply of the breathing gas from the ventilator based on a preselected ventilation mode into the endotracheal tube and thence into the patient at the initiation of the inhalation effort, the regulating means, responsive to the monitoring means, for automatically and proportionally regulating the supply of the breathing gas provided to the patient by the gas delivery means so that the pressure of the breathing gas proximate the distal end of the endotracheal tube is maintained at a predetermined baseline pressure that is at least zero throughout the inhalation effort.

21. The medical ventilator of claim 20, wherein the monitoring means detects when the pressure of the breathing gas proximate the distal end of the endotracheal tube drops below the predetermined baseline pressure during the inhalation effort of the patient and generates a response signal thereof.

22. The medical ventilator of claim 21, wherein the regulating means is responsive to the response signal to increase the supply of the breathing gas delivered by the medical ventilator so that the pressure of the breathing gas proximate the distal end of the endotracheal tube is maintained at the predetermined baseline pressure.

23. The medical ventilator of claim 20, wherein the monitoring means detects when the pressure of the breathing gas proximate the distal end of the endotracheal tube exceeds the predetermined baseline pressure and generates a termination signal thereof.

24. The medical ventilator of claim 23, wherein the regulating means is responsive to the termination signal to decrease the supply of the breathing gas delivered by the medical ventilator so that the pressure of the breathing gas at the distal end of the endotracheal tube is maintained at the predetermined baseline pressure.

25. The medical ventilator of claim 20, wherein the pressure sensing means is disposed in a flow path of the breathing gas within the endotracheal tube.

26. The medical ventilator of claim 25, wherein the pressure sensing means for sensing the pressure of the breathing gas is located proximate the distal end of the endotracheal tube.

27. The medical ventilator of claim 20, wherein the gas delivery means comprises a pneumatic system having at least one electrically coupled actuator, in fluid communication with the gas source for providing the supply of the breathing gas upon command.

28. The medical ventilator of claim 27, wherein the actuator regulates a pressure, a flow rate, or a combination of both to regulate the supply of the breathing gas provided by the ventilator to the patient.

29. The medical ventilator of claim 27, wherein the regulating means comprises at least one driver circuit electrically coupled to the monitoring means and to each actuator, wherein the driver circuit adjusts the actuator based on electrical signals received from the monitoring means, thereby regulating the supply of the breathing gas provided by the gas delivery means.

30. The medical ventilator of claim 20, wherein the monitoring means comprises a microprocessor having a memory means for storing signal data.

31. A respiratory support system for a patient, comprising:

a. an endotracheal tube, the endotracheal tube having a distal end adapted for positioning within the patient's trachea;

b. a pressure sensor disposed in a flow path of the breathing gas within the endotracheal tube which measures the pressure of the gas proximate the pressure sensor and which provides a pressure signal representative thereof, wherein the pressure sensor is located proximate the distal end of the endotracheal tube;

c. a medical ventilator for providing breath support to the patient, the medical ventilator adapted for connection to a source of one or more breathing gases and to the endotracheal tube, the medical ventilator having a processor responsive to the gas pressure signal generated by the pressure sensor and having at least one actuator, responsive to the processor, to regulate a supply of the breathing gas provided by the ventilator to the patient, wherein the processor has a program for delivering the supply of the breathing gas to the patient at the initiation of an inhalation effort based on a preselected ventilation mode and a program for automatically and proportionally controlling the supply of the breathing gas delivered thereto the endotracheal tube to substantially maintain the pressure of the breathing gas proximate the distal end of the endotracheal tube at a predetermined baseline pressure that is at least zero throughout an inhalation effort of the patient.

32. The respiratory support system of claim 31, wherein the processor detects when the pressure of the gas within the endotracheal tube drops below the predetermined baseline pressure and generates a response signal thereof.

33. The respiratory support system of claim 32, wherein the actuator is responsive to the response signal to increase the supply of the breathing gas provided by the medical ventilator so that the pressure of the breathing gas proximate the distal end of the endotracheal tube is maintained at the predetermined baseline pressure.

34. The respiratory support system of claim 32, wherein the processor detects when the pressure of the breathing gas within the endotracheal tube exceeds the predetermined baseline pressure and generates a termination signal thereof.

35. The respiratory support system of claim 34, wherein the actuator is responsive to the termination signal to decrease the supply of the breathing gas provided by the ventilator so that the pressure of the breathing gas at the distal end of the endotracheal tube is maintained at the predetermined baseline pressure.

36. The respiratory support system of claim 31, wherein the actuator regulates a pressure, a flow rate, or a combination of both to regulate the supply of the breathing gas provided by the ventilator to the patient.

* * * * *